(12) United States Patent
Giovannone et al.

(10) Patent No.: US 9,750,815 B2
(45) Date of Patent: Sep. 5, 2017

(54) COMPOSITION COMPRISING SHELLAC AND/OR A SALT THEREOF AND SODIUM STARCH GLYCOLATE

(75) Inventors: Daniele Giovannone, Frosinone (IT); Carlo De Angelis, Fontana Liri (IT)

(73) Assignee: GNOSIS SPA, Milan (IT)

( * ) Notice: Subject to any disclaimer, the term of this patent is extended or adjusted under 35 U.S.C. 154(b) by 0 days.

(21) Appl. No.: 13/812,465

(22) PCT Filed: Jun. 30, 2011

(86) PCT No.: PCT/IB2011/052896
§ 371 (c)(1),
(2), (4) Date: Jan. 25, 2013

(87) PCT Pub. No.: WO2012/014104
PCT Pub. Date: Feb. 2, 2012

(65) Prior Publication Data
US 2013/0133551 A1    May 30, 2013

Related U.S. Application Data

(60) Provisional application No. 61/367,720, filed on Jul. 26, 2010.

(30) Foreign Application Priority Data

Jul. 27, 2010 (IT) ................ MI2010A1386

(51) Int. Cl.
*A61K 47/44* (2017.01)
*A61K 9/48* (2006.01)
(Continued)

(52) U.S. Cl.
CPC .............. *A61K 47/44* (2013.01); *A61K 9/282* (2013.01); *A61K 9/286* (2013.01); *A61K 9/4808* (2013.01);
(Continued)

(58) Field of Classification Search
USPC ...... 106/162.81, 214.2, 215.4; 424/479, 475, 424/480, 481
See application file for complete search history.

(56) References Cited

U.S. PATENT DOCUMENTS 6,475,493 B1 * 11/2002 Mulye .................. A61K 9/5078
424/400
7,425,342 B2 * 9/2008 Kannar .......................... 424/754
(Continued)

FOREIGN PATENT DOCUMENTS

CN       1260172 A        7/2000
DE    102008063800 A1 *   6/2010  .............. A61Q 5/10
(Continued)

OTHER PUBLICATIONS

Explotab Low pH product sheet revision 2, JRS Pharma LP, Mar. 2003.*
(Continued)

*Primary Examiner* — Melvin C Mayes
*Assistant Examiner* — James Corno
(74) *Attorney, Agent, or Firm* — Wenderoth, Lind & Ponack, L.L.P.

(57) ABSTRACT

The object of the present invention is a composition comprising shellac and/or a salt thereof and sodium starch glycolate and at least one physiologically acceptable excipient and a process for obtaining it.

30 Claims, 1 Drawing Sheet

(51) Int. Cl.
     *A61K 9/28*      (2006.01)
     *A61K 9/50*      (2006.01)
     *A61K 31/192*    (2006.01)
     *A61K 31/4439*   (2006.01)
     *A61K 35/744*    (2015.01)
     *A61K 47/36*     (2006.01)
     *A61K 9/16*      (2006.01)

(52) U.S. Cl.
     CPC .......... *A61K 9/4816* (2013.01); *A61K 9/4891* (2013.01); *A61K 9/5015* (2013.01); *A61K 9/5036* (2013.01); *A61K 9/5078* (2013.01); *A61K 31/192* (2013.01); *A61K 31/4439* (2013.01); *A61K 35/744* (2013.01); *A61K 47/36* (2013.01); *A61K 9/1611* (2013.01); *A61K 9/1623* (2013.01); *A61K 9/485* (2013.01); *A61K 9/4858* (2013.01)

(56) References Cited

U.S. PATENT DOCUMENTS

| | | | |
|---|---|---|---|
| 2004/0103821 A1* | 6/2004 | Shobu et al. | 106/237 |
| 2005/0031775 A1 | 2/2005 | Signorino et al. | |
| 2007/0071821 A1* | 3/2007 | Young | 424/470 |
| 2009/0252767 A1* | 10/2009 | Durig et al. | 424/400 |

FOREIGN PATENT DOCUMENTS

| | | |
|---|---|---|
| JP | S62-223182 | 10/1987 |
| JP | 2005-508331 A | 3/2005 |
| WO | WO0176392 | 10/2001 |
| WO | WO0200205 A1 | 1/2002 |
| WO | WO2009064429 | 5/2009 |
| WO | 2010/075290 A1 | 7/2010 |
| WO | 2010/075561 A1 | 7/2010 |
| WO | 2010/080977 A2 | 7/2010 |
| WO | 2010/132072 A1 | 11/2010 |
| WO | 2011/026240 A1 | 3/2011 |

OTHER PUBLICATIONS

Ragheb et al. ("Preparation and Characterization of Carboxymethyl Starch (CMS) Products and Their Utilization in Textile Printing," Starch 49(6), pp. 238-245, Oct. 2006).*
Green et al. ("Which Starch Fraction is Water-Soluble, Amylose or Amylopectin?" Journal of Chemical Education 52(11), pp. 729-730, Nov. 1975).*
McNeil Consumer Healthcare Division; McNeil-PPC, Inc., Tylenol Arthritis Pain Drug Facts Sheet.
Erich Brunner, Rote Liste 2009.
PCT, Notification Concerning Submission, Obtention or Transmittal of Priority Document.
PCT Request.
Drugs.com, Tylenol Allergy Multi-Symptom Nighttime (McNeil Consumer Healthcare DivMcNeil-PPC) fact sheet.
Galephar Pharmaceutical Research Inc., "Lipofen (fenofibrate capsules)," Jan. 2006, Juncos, Puerto Rico 00777-3873.
Chemical Abstracts Service, Technical Report Registry, CAS RN 9057-06-1, Entered STN Nov. 16, 1984, copyright 2014.
Chemical Abstracts Service, Technical Report Registry, CAS RN 9063-38-1, Entered STN Nov. 16, 1984, copyright 2014.
USPATFULL Database on STN, Technical Report for Kannar, David, Odorless garlic supplement comprising an enteric coating and a deodorizing layer, 2004:220940.
AU6887787 (JPS61-223182) for translation purposes.
WO03026637 A2 (JP2005-508331) for translation purposes.

* cited by examiner

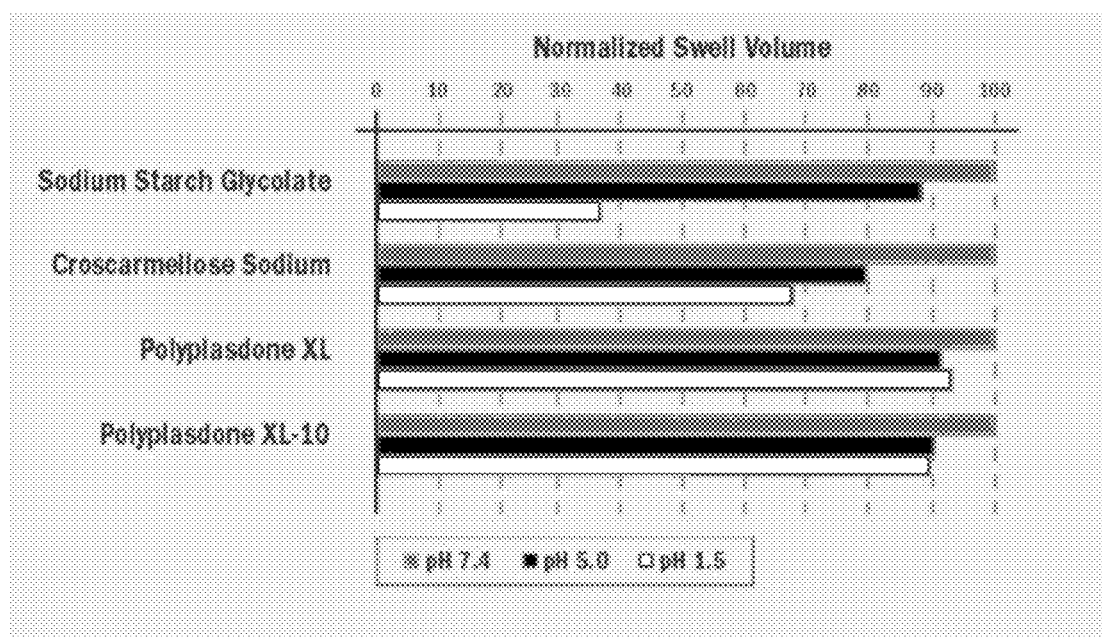

COMPOSITION COMPRISING SHELLAC AND/OR A SALT THEREOF AND SODIUM STARCH GLYCOLATE

This application claims priority to PCT International Application Number PCT/IB2011/052892, having filing date of Jun. 30, 2011, which claims application to Italian application No. MI2010A001386 having priority date of Jul. 27, 2010, and U.S. Application No. 61/367,720 having priority date of Jul. 26, 2010. Each of these applications are herein incorporated by reference and priority is hereby claimed to the priority date of each of these applications.

The object of the present invention is a composition comprising shellac and/or a salt thereof and sodium starch glycolate and at least one physiologically acceptable excipient.

Said shellac and/or a salt thereof according to the present invention can be aqueous or alcoholic, preferably aqueous.

Said shellac salt according to the present invention can be a potassium salt, an ammonium salt or a salt of a basic amino acid and/or a mixture thereof, wherein said basic amino acid is preferably selected from among arginine, lysine, ornithine and/or a mixture thereof.

The composition according to the present invention is preferably a coating composition for solid oral formulations, more preferably tablets (acidic, neutral, basic, according to the nature of the active ingredient and/or nutraceutical, dietetic or food supplement contained in them), capsules, pellets, granulates and/or microgranulates.

Said coating composition according to the present invention is preferably a gastroresistant coating composition.

According to a preferred embodiment of the present invention, said composition can constitute a system ready for use for pharmaceutical, dietetic, nutraceutical or food coatings.

STATE OF THE ART

It is known that in many cases it is necessary for pharmaceutical, dietetic, nutraceutical or food solid oral formulations to be able to pass through the stomach intact, in order to release their content in the gastrointestinal tract. This is the case, for example, when the active ingredient and/or the nutraceutical, dietetic or food supplement is made inactive by the gastric juice or irritates the gastric wall; in order to make the active ingredient and/or nutraceutical, dietetic or food supplement reach the intestine in a concentration such as to be able to act locally or to obtain greater absorption of the active ingredient and/or of the nutraceutical, dietetic or food supplement through a limitation of the area in which it is released.

This purpose can be obtained by coating the pharmaceutical, dietetic, nutraceutical or food solid oral formulations with a gastroresistant (enteric) coating.

Enteric coatings commonly consist of materials with characteristics of: pH-dependent solubility, between pH 5 and 7; quick dissolving in a non-gastric medium; insensitivity to variations in ionic force; stability in storage.

In the pharmaceutical industry enteric coatings are widely used, with a vast choice of enteric materials like hydroxypropyl methylcellulose phthalate (HPMCP), polymers or copolymers of acrylic or methacrylic acid (for example Eudragit™), cellulose acetate phthalate (CAP) and polyvinyl acetate phthalate (PVAP). All of these enteric materials were developed to provide a vast range of coatings that are soluble in organic solvents or in aqueous dispersions.

However, the approval for use of these materials in the pharmaceuticals industry has required numerous application studies and rigorous testing, using an amount of resources that is unfeasible in the food sector. Consequently, these enteric materials are not approved for food use and cannot be used legally as enteric coatings for non-pharmaceutical solid oral formulations, including nutraceutical or dietetic supplements. There are very few materials that can be used as enteric coating in the nutraceutical, dietetic or food field.

One example is Zein, a prolamine obtained from corn used in the past as a coating material, but which has very poor enteric properties as well as numerous problems connected to the coating techniques, to costs and to environmental impact.

Another example of a material that can be used as an enteric coating in the nutraceutical, dietetic or food field is shellac.

Shellac is a natural substance, acidic in nature, recognised as GRAS or "Generally Recognized As Safe" by the American Food and Drug Administration (FDA). This makes it suitable for use as a coating for drugs, nutraceuticals or dietetics in solid oral formulations, as well as for food products.

Shellac is the purified product of lac, a natural resinous oligomer with molecular weight of about 1000 D, secreted by the parasitic insect *Kerria lacca*. It is made up of polyesters, mainly aleuritic acid, shellolic acid, and a small amount of aliphatic acids, with variable composition according to the species of insects as well as the tree hosting them from which the raw material is objected. It is also a known filming agent, thanks to its excellent filmogenous properties, its shininess and its low permeability to gas and water vapour.

Although it has these advantages, the use of shellac as pharmaceutical, nutraceutical, dietetic or food excipient is low with respect to that of synthetic or partially synthetic polymers (for example polymethacrylates and cellulose derivatives).

This is due mainly to problems of instability linked to shellac, which over time tends to degenerate, modifying its physical-chemical properties and gradually losing or increasing the properties of gastroresistance.

Conventional films of shellac, prepared in alcohol solutions, indeed display a progressive and pronounced hardening, induced by a continuous polymerisation process. This translates, as well as into the partial separation of the coating film from the core containing an active ingredient and/or a nutraceutical, dietetic or food supplement, into a loss of gastric resistance and into a decreased solubility at the level of the intestinal fluids, which can cause great changes in the dissolving profiles of the active ingredient and/or of the nutraceutical, dietetic or food supplement. Indeed, considering the poor solubility in water of shellac and its dissolving at a relatively high pH (about 7.3), a further reduction of solubility in the intestinal fluids can cause an incomplete release of the active ingredient and/or of the nutraceutical, dietetic or food supplement by the pharmaceutical and/or nutraceutical, dietetic or food form.

Moreover, the increased permeability to gastric fluid caused by the loss of gastric resistance of the film of shellac can cause the degradation of acid-labile active ingredients and/or nutraceutical, dietetic or food supplements.

In order to overcome such limitations, alternative formulations in aqueous solution have been proposed in which shellac is combined with hydroxides of alkaline metals, in particular sodium or ammonium hydroxide.

Although these films in aqueous solution display better stability with respect to conventional films in alcohol solution, the drawbacks due to ageing still remain strongly linked both to the quality of the shellac used (origin, refining process) and to the chemical-physical characteristics of the cores to be coated.

Numerous technologies and formulations have been studied as possible solutions to the problems connected to shellac-based coating agents, but even through the combination of these different techniques it has not yet been possible to solve the existing problems without producing new ones.

US20070071821 describes the association between a shellac salt and an alginate for the formulation of a coating with improved enteric properties, entirely made up of materials approved for food use. This combination, whilst being advantageous in terms of functionality with respect to other shellac salts in aqueous solution, does not yet effectively overcome the limitations of shellac-based coatings linked to ageing of the product.

The family of patents referring to US20040103821 describes a shellac coating agent in aqueous solution, comprising a basic amino acid and/or a basic phosphate. Also in this case, however, the shellac films obtained are relatively insensitive to pH and disintegrate in two or three hours, irrespective of the acidity or alkalinity of the solution, instead behaving like erodible films that dissolve as a function of the time. In particular, it displayed limitations linked both to the stability and to the functionality of the coating in relation to the chemical-physical characteristics of the material coated.

There is therefore a need to provide a composition accepted in the field of pharmaceuticals, as well as of nutraceuticals, dietetics or foods that has improved ability to control release and improved stability over time.

DESCRIPTION it has now been surprisingly found that a composition containing shellac in combination with sodium starch glycolate overcomes the limitations of the state of the art and has optimal properties in terms of appearance, hardness, adhesion and stability.

The term "shellac", according to the present invention, refers to a natural polymer equipped with thermoplastic properties, also known under the name E 904.

Sodium starch glycolate is a sodium salt obtained from potato starch, approved by the Food and Drug Administration (FDA) as a disintegrant used both in pharmaceutical and food products. Therefore it is an excipient present both in the GRAS list in the USA and in the list of products that can be used as a food additive in Europe.

It is known in literature that the source of starch, the size of the particles, the viscosity, the degree of substitution and of cross-linking have an influence on the functionality of sodium starch glycolate.

Its main function is to be a superdisintegrant of solid oral formulations, preferably tablets.

The term "superdisintegrant" according to the present invention refers to a disintegrant of the second generation, characterised by particularly effective activity.

The action mechanism with which it operates is drawing water inside the solid pharmaceutical, nutraceutical, dietetic or food form causing the subsequent swelling and development of a disintegration force inside the aforementioned form.

The lowering of the pH of the solution in which it is dissolved, or dispersed, to very acidic values reduces the speed and degree of absorption of the liquid by the sodium starch glycolate and consequently its disintegrant power.

FIG. 1 shows the difference in disintegrant power as a function of the pH of some of the most well-known superdisintegrants. From the analysis of FIG. 1 it is clear that sodium starch glycolate is the only one of the selected disintegrants having a low disintegrant power at acidic pH. On the other hand, it displays a high disintegrant power at pH neutral.

It has now been surprisingly found that, when shellac and/or a salt thereof is added to it, sodium starch glycolate forms a composition resistant to acids (for example in an environment with pH between 1 and 5) capable of easily disintegrating as soon as the conditions become slightly alkaline (for example in an environment with pH between 6 and 7), thus performing the functions of an excellent enteric excipient.

The presence of sodium starch glycolate also makes it possible to stabilise the shellac and/or salt thereof over time thanks to the fact that it minimises its polymerisation and hardening. In this way, the chemical-physical characteristics of the shellac and/or of a salt thereof remain stable over time ensuring a more homogeneous profile of the release characteristics of the active ingredient and/or nutraceutical, dietetic or food supplement. No other known disintegrant for food, nutraceutical, dietetic or food use allows the same advantages to be obtained.

The object of the present invention is thus a composition comprising shellac and/or a salt thereof and sodium starch glycolate and at least one physiologically acceptable excipient.

The shellac and/or a salt thereof according to the present invention can be aqueous or alcoholic, preferably aqueous.

The shellac salt according to the present invention is preferably selected from among a potassium salt, an ammonium salt or a salt of a basic amino acid and/or a mixture thereof, where said basic amino acid is preferably selected from among arginine, lysine, ornithine and/or a mixture thereof.

The most preferred basic amino acid according to the invention is arginine.

The composition according to the present invention is preferably a coating composition for solid oral formulations, more preferably a gastroresistant coating composition (film). Solid oral formulations according to the invention preferably refer to tablets (acidic, neutral, basic), capsules, pellets, granulates and/or microgranulates.

Said composition displays a functionality highly sensitive to pH, irrespective of the chemical-physical characteristics of the material coated and it ensures homogeneity of gastroresistance over time.

The composition containing shellac and/or a salt thereof and sodium starch glycolate of the invention disintegrates little in an acidic environment and easily at neutral/alkaline pH.

According to a preferred embodiment of the present invention, said composition can constitute a system ready for use for pharmaceutical, nutraceutical, dietetic or food coatings.

A "system ready for use" according to the present invention refers to a mixture that is either liquid (for example a solution) or semi-solid (for example a suspension or dispersion) that can be applied directly on the solid oral form to be coated, without the need to reformulate the final mixture.

Sodium starch glycolate is commercially available as type A and type B, which differ in their different sodium content.

Indeed, type A contains from 2.8 to 4.2% by weight of sodium with respect to the total weight, whereas type B contains from 2.0 to 3.4% by weight of sodium with respect to the total weight. The pH of an aqueous dispersion containing 3.3% sodium starch glycolate by weight varies from 3 to 5 or from 5.5 to 7.5 according to the type used.

In the composition according to the present invention both sodium starch glycolate of type A and of type B and/or a mixture of them can be used.

In the composition according to the present invention the sodium starch glycolate is preferably used in the form of powder with granulometry of between 0.5 and 200 micron, more preferably between 10 and 50 micron.

In the compositions according to the present invention, the shellac and/or a salt thereof is preferably contained in an amount between 1 and 99% by weight with respect to the total weight, more preferably between 50 and 95% by weight with respect to the total weight.

In the compositions according to the present invention, the sodium starch glycolate is preferably contained in an amount between 0.05 and 70% by weight with respect to the total weight, more preferably between 0.1% and 50% by weight with respect to the total weight.

According to a preferred embodiment of the invention, the shellac and/or a salt thereof and the sodium starch glycolate are present in equal amounts.

The composition according to the present invention is preferably formulated in the forms of a solution and/or suspension and/or powder to be reconstituted in water, more preferably in the form of an aqueous suspension.

The composition according to the present invention can also be formulated in the form of a solution and/or suspension and/or powder to be reconstituted in water, preferably in the form of a spray suspension.

The composition according to the present invention can contain one or more further physiologically acceptable excipients, preferably plasticizers, suspension agents or glidants and/or dilutants.

Plasticizers according to the invention are preferably selected from among triethyl citrate, polyethylene glycol, polypropylene glycol, glycerol monostearate, polyols, glycerine, vegetable oils and/or a mixture thereof.

Said plasticizers are preferably added in an amount between 2 and 50% by weight with respect to the total weight, preferably to optimise the flexibility of the composition.

Suspension agents or glidants according to the invention are preferably selected from among silica, precipitated silica, talc and/or a mixture thereof.

Dilutants according to the invention are preferably selected from among talc, titanium dioxide and/or a mixture thereof.

A further object of the present invention is a process for preparing the composition as described above that comprises the steps of:
a) preparing the solution of shellac and/or a salt thereof, solution A;
b) preparing the aqueous suspension of sodium starch glycolate, suspension B;
c) mixing solution A and suspension B.

In the preparation of solution A it is possible to use all types of shellac known on the market.

According to the invention, in step a) the shellac and/or a salt thereof is dissolved in a polar solvent, preferably a $C_1$-$C_4$ alcohol, more preferably methanol, ethanol, isopropanol, n-propanol, and the like, or water and/or in a mixture thereof, even more preferably it is dissolved in water.

In a more preferred embodiment of the present invention the shellac is dissolved in water in the form of ammonium, potassium or basic amino acid salt.

Preferably, said step a) according to the invention is carried out under stirring and/or heat.

The term "heat" according to the present invention, refers to a temperature between room temperature and the boiling temperature of the solvent used.

According to the invention, in step c) the shellac and/or a salt thereof is added to the aqueous suspension of sodium starch glycolate, suspension B, to give a composition that, applied on any type of solid oral formulation, preferably tablets (acidic, neutral, basic), capsules, pellets, granulates and/or microgranulates, forms a coating that disintegrates in slightly alkaline conditions (for example in an environment with pH between 6 and 7).

In a preferred embodiment of the present invention, the shellac is heated in water, under stirring, to a temperature of between 50 and 100° C., preferably between 70 and 75° C. Then the amino acid and the aqueous suspension of sodium starch glycolate, obtained by dispersing the sodium starch glycolate in water, are added. Again under stirring, the temperature is brought to about 80° C. and it is stirred again for about 30 minutes. The solution thus obtained is then cooled.

In a further preferred embodiment of the present invention said process is carried out at a temperature of between 50 and 100° C., preferably between 50 and 80° C.

The pH of the mixture, or one of the components inside the mixture, can be adjusted and/or selected to make said solution or suspension more manageable.

The solution of shellac and/or of a salt thereof and sodium starch glycolate can, after possible mixing with one or more further excipients according to the present invention, be applied onto solid oral formulations through the methods of the prior art.

Preferred forms of application according to the present invention are film-coating in coating pans and/or film-coating of the pellets and/or enteric microincapsulation on a fluid bed and/or spraying.

A further object of the present invention is the use of the composition containing shellac and/or a salt thereof and sodium starch glycolate as described above for coating pharmaceutical, nutraceutical, dietetic or food solid oral formulations.

The term "capsule" according to the present invention is intended to include rigid capsules, soft capsules, pastilles, losenges and/or pills.

A further object of the present invention is a solid oral formulation coated with the composition comprising shellac and/or a salt thereof and sodium starch glycolate as described above. Preferably, the solid oral formulation coated according to the invention is a gastroresistant formulation in which said gastroresistance is given by the coating composition containing shellac and/or a salt thereof and sodium starch glycolate mentioned above (film).

Solid oral formulation according to the invention preferably refer to tablets (acidic, neutral, basic), capsules, pellets, granulates and/or microgranulates.

The coated pharmaceutical, nutraceutical, dietetic or food solid oral formulation according to the invention has the advantage of being stable over time and it ensures a homogeneous release of the active ingredient and/or of the nutraceutical, dietetic or food supplement.

Therefore, the presence of the composition containing shellac and/or a salt thereof and sodium starch glycolate leads to improved stability, improved characteristics of release and disintegration of the solid oral formulation coated by it.

The coated composition of the invention can contain one or more active ingredients and/or nutraceutical, dietetic or food supplements and at least one physiologically acceptable adjuvant.

Examples of active ingredients and/or nutraceutical or dietetic supplements that can be coated with the composition of the present invention are for example SAMe (S-adenosyl methionine) and/or its physiologically acceptable salts, lansoprazole, pantoprazole, ibuprofen, lactic ferments, NADH or NAD (nicotinamide adenine dinucleotide), SOD (superoxide dismutase), nattokinase, preferably SAMe and/or its physiologically acceptable salts.

According to a preferred embodiment the coated composition of the invention comprises a core containing at least one active ingredient and/or nutraceutical, dietetic or food supplement and at least one physiologically acceptable adjuvant, surrounded externally by the composition containing shellac and/or a salt thereof and sodium starch glycolate as described above.

Said physiologically acceptable adjuvant is preferably selected from among dilutants, binders, disintegrants, stabilizers, glidants or lubricants.

Said dilutants include, for example, lactose, starches, microcrystalline cellulose, calcium phosphate and calcium carbonate.

Said binders include, for example, PVP (polyvinyl pyrrolidone), gelatine, cellulose derivatives (for example HPMC, CMC, MC), tragacanth, gum arabic and polyethylene glycols.

Said disintegrants include, for example, corn starch, cellulose (for example, microcrystalline cellulose, carboxymethyl cellulose (CMC), croscarmellose), alginates and polyvinyl pyrrolidones (for example crospovidone).

Said stabilizers include, for example, calcium or magnesium oxide, calcium or magnesium hydroxide, calcium or magnesium chloride.

Said glidants include, for example, talc, colloidal silica and precipitated silica.

Said lubricants include, for example, stearates, stearic acid, talc, wax and other fatty substances.

From the experimental data of the Examples given hereafter, it can be seen that the disintegration times of the formulations according to the present invention at pH 6.8 are within specifications according to the disintegration test described in the USP current edition and that the variation of the disintegration at pH 6.8 is constant over time after the samples are conserved at 40° C. for 6 months.

The following examples are intended to better explain the present invention, without in any way limiting it.

EXAMPLES

Stability Tests of the Gastroresistant Film on the End Product

The stabilities at 40° C. and 75% relative humidity (R.H.) (STRESS TEST) and at room temperature in the long term (SHELF LIFE) of the compositions of the Examples were evaluated through the variations of the disintegration time of the gastroresistant coating object of the present invention both at pH 1.2 and at pH 6.8 according to what is described in United States Pharmacopeia USP, current edition.

Moreover, the water content (K.F.), the active ingredient content and the total impurity content were determined to check that the tablets did not undergo particular variations such as to jeopardise the gastroresistance test.

Stress Test

The tablets were packaged in capped and sealed glass flasks so as to reproduce the final packaging conditions for products containing these active ingredients (in general, aluminium/aluminium blister pack).

The samples thus prepared were conserved for six months in thermostated oven at a temperature of 40±2° C. and 75% R.H.

Samples coming from different batches were used for the tablets of the Examples where each sample, for each batch, was sampled after 0, 1, 3 and 6 months.

Shelf Life

The tablets were packaged in capped and sealed glass flasks so as to reproduce the final packaging conditions (in general, aluminium/aluminium blister pack).

The samples were selected according to the same ways and amounts described for the stress test and conserved in a thermostated environment at a temperature of 25±2° C. and humidity equal to 60% R.H.

Samples coming from one batch were used for the Examples, where each sample was sampled after 0, 3, 6, 12 months.

All of the examples refer to the preparation of a standard laboratory batch of 2.00 kg of tablets.

Example 1: 30 mg Gastroresistant Lansoprazole Tablets

| | |
|---|---|
| A. Lansoprazole | 30.00 mg |
| B Microcrystalline cellulose. | 70.00 mg |
| C. Mannitol | 80.00 mg |
| D. Sorbitol | 50.00 mg |
| E. PVP CL | 20.00 mg |
| F. Silicon dioxide | 2.00 mg |
| G. Stearic acid | 10.00 mg |
| H. Magnesium stearate | 2.00 mg |
| Total core weight | 264.00 mg |
| I. Arginine Shellac | 30.00 mg |
| L. Sodium starch glycolate | 6.0 mg |
| M. Titanium dioxide | 5.00 mg |
| N. Talc | 10.00 mg |
| O. Triethyl citrate | 5.00 mg |
| P. Precipitated silica | 2.00 mg |
| Q. Curcumin | 0.050 mg |
| Total tablet weight | 322.05 mg |

1. Mixing

The working environment is conditioned at a temperature of 25° C. and at a relative humidity value equal to about 40% R.H. Then A, B, C, D, E, F, G and H are transferred in the amounts indicated above, into the mixer, leaving them under stirring for about 30 minutes. At the end of such an operation, the resulting mixture is transferred into dry recipients, still controlling humidity and temperature.

2. Compression

The final compression of the mixture is carried out through a rotary machine equipped with punches of suitable shape and size for the weight of the core, producing tablets with a hardness of at least 20 KP. The tablets produced have a hardness of between 20 and 25 Kp.

Friability: ≤1.0%; disintegration time: ≤15 minutes (measured according to the method described in U.S.P. Current edition).

3. Film-Coating of the Tablet

In a suitably sized recipient the shellac is dissolved with the arginine base at 60° C., the sodium starch glycolate is added and it is brought to 80° C. until a solution at 20% p/v of the arginine schellac salt with 4% sodium starch glycolate in suspension. Thereafter, under constant stirring, the triethyl citrate is slowly added.

In another steel recipient again equipped with a stirrer, the talc, the titanium dioxide, the precipitated silica and the curcumin are dispersed in 4.0 l of deionized water. The resulting suspension is poured into the arginine shellac solution, washing the recipient with about 1.0 l of deionized water, then diluting with another 4.0 l of deionized water. The enteric coating is carried out at a temperature of the cores of 45° C. and, once the gastroresistant coating is complete, it is left to dry for another 10 minutes still at 45° C. Finally, it is necessary to wait until the temperature lowers to 32-33° C. so as to be able to start emptying the coating pan, taking care to keep the tablets in suitable bags that are impermeable to humidity. All of the tests foreseen by the quality specifications are carried out on them.

TABLE 1

Stress test of Batches 001 and 014-30 mg lansoprazole tablets (quali/quantitative composition from Example 1)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 001 (20/0) | 0.55 | 0.12 | 30.4 | 60.00 | 27.00 |
| 001A (40/1) | 0.45 | 0.18 | 30.2 | 60.00 | 28.00 |
| 001B (40/3) | 0.65 | 0.16 | 30.0 | 60.00 | 30.00 |
| 001C (40/6) | 0.44 | 0.19 | 30.1 | 60.00 | 29.00 |
| 014 (20/0) | 0.48 | 0.23 | 29.9 | 60.00 | 25.00 |
| 014A (40/1) | 0.43 | 0.22 | 30.1 | 60.00 | 26.00 |
| 014B (40/3) | 0.56 | 0.32 | 29.8 | 60.00 | 27.00 |
| 014C (40/6) | 0.51 | 0.28 | 29.7 | 60.00 | 28.00 |

[1]Temperature (° C.)/time (months);
[2]Disintegration test according to USP current edition.

The data in Table 1 shows that in the presence of sodium starch glycolate, the disintegration times at pH 6.8 are within specifications according to the disintegration test described in USP current edition and the variation of the disintegration again at pH 6.8 is constant over time after the samples are conserved at 40° C. for 6 months.

TABLE 2

Shelf life of Batch 027-30 mg lansoprazole tablets (quali/quantitative composition of Example 1)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 027 (20/0) | 0.33 | 0.25 | 30.23 | 60.00 | 27.00 |
| 027A (25/3) | 0.35 | 0.33 | 31.21 | 60.00 | 27.00 |
| 027B (25/6) | 044 | 0.38 | 29.83 | 60.00 | 29.00 |
| 027C (25/12) | 0.54 | 0.31 | 29.79 | 60.00 | 31.00 |

[1]Temperature (° C.)/time (months);
[2] Disintegration test according to USP current edition.

Example 2: 30 mg Gastroresistant Lansoprazole Tablets without Sodium Starch Glycolate

| | |
|---|---|
| A. Lansoprazole | 30.00 mg |
| B Microcrystalline cellulose | 70.00 mg |
| C. Mannitol | 80.00 mg |
| D. Sorbitol | 50.00 mg |
| E. PVP CL | 20.00 mg |
| F. Silicon dioxide | 2.00 mg |
| G. Stearic acid | 10.00 mg |
| E. Magnesium stearate | 2.00 mg |
| Total core weight | 264.00 mg |
| F. Arginine Shellac | 30.00 mg |
| G. Titanium dioxide | 5.00 mg |
| H. Talc | 10.00 mg |
| I. Triethyl citrate | 5.00 mg |
| L. Precipitated silica | 2.00 mg |
| M. Curcumin | 0.050 mg |
| Total tablet weight | 316.05 mg |

TABLE 3

Stress test of Batches 002 and 015-30 mg lansoprazole tablets (quali/quantitative composition of Example 2)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 002 (20/0) | 0.59 | 0.23 | 30.32 | 60.00 | 44.00 |
| 002A (40/1) | 0.55 | 0.18 | 30.64 | 60.00 | 53.00 |
| 002B (40/3) | 0.61 | 0.26 | 30.15 | 60.00 | 63.00 |
| 002C (40/6) | 0.74 | 0.27 | 29.71 | 60.00 | 69.00 |
| 015 (20/0) | 0.66 | 0.28 | 30.56 | 60.00 | 47.00 |
| 015A (40/1) | 0.61 | 0.23 | 30.99 | 60.00 | 58.00 |
| 015B (40/3) | 0.67 | 0.29 | 30.43 | 60.00 | 65.00 |
| 015C (40/6) | 0.73 | 0.37 | 30.03 | 60.00 | 79.00 |

[1]Temperature (° C.)/time (months);
[2]Disintegration test according to USP current edition.

The data in Table 2 shows that in the absence of sodium starch glycolate, the disintegration times at pH 6.8 (according to USP current edition) are considerably longer at time zero, and the variation thereof again at pH 6.8 is not constant over time after the samples are conserved at 40° C. for 6 months.

TABLE 4

Shelf life of Batch 028-30 mg lansoprazole tablets without sodium starch glycolate (quali/quantitative composition of Example 2)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 028 (20/0) | 0.54 | 0.38 | 31.34 | 60.0 | 46.00 |
| 028A (25/3) | 0.51 | 0.29 | 31.23 | 60.0 | 50.00 |
| 028B (25/6) | 0.56 | 0.34 | 30.21 | 60.0 | 55.00 |
| 028C (25/12) | 0.69 | 0.39 | 29.67 | 60.0 | 69.00 |

[1]Temperature (° C.)/time (months);
[2]Disintegration test according to USP current edition.

Example 3: 40.0 mg Gastroresistant Sodium Pantoprazole Tablets

| | |
|---|---|
| A. Sodium pantoprazole | 40.00 mg |
| C. Maltodextrine | 70.00 mg |
| D. Mannitol | 50.00 mg |
| E. Calcium sulphate dihydrate | 40.00 mg |
| F. Calcium phosphate dihydrate | 40.00 mg |
| G. Magnesium stearate | 20.00 mg |
| H. Dried malic acid | 80.00 mg |
| I. Stearic acid | 40.00 mg |
| Total core weight | 380.00 mg |
| L. Arginine Shellac | 30.00 mg |
| M. Sodium starch glycolate | 6.0 mg |
| N. Titanium dioxide | 5.00 mg |
| O. Talc | 10.00 mg |
| P. Triethyl citrate | 5.00 mg |
| Q. Precipitated silica | 2.00 mg |
| R. Yellow tartrazine | 0.050 mg |
| Total tablet weight | 438.05 mg |

The tablets were prepared according to the ways described in Example 1 using the components and the amounts indicated above.

The cores, due to the presence of malic acid, are characterised by having an acidic pH to test the behaviour of the film for this kind of type.

TABLE 5

Stress test of Batches 003 and 016-40 mg sodium pantoprazole tablets (quali/quantitative composition of Example 3)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 003 (20/0) | 0.67 | 0.42 | 41.53 | 60.00 | 25.00 |
| 003A (40/1) | 0.85 | 0.38 | 41.25 | 60.00 | 26.00 |
| 003B (40/3) | 0.65 | 0.46 | 40.04 | 60.00 | 31.00 |
| 003C (40/6) | 0.84 | 0.59 | 40.11 | 60.00 | 28.00 |
| 016 (20/0) | 0.76 | 0.51 | 40.59 | 60.00 | 26.00 |
| 016A (40/1) | 0.88 | 0.45 | 41.02 | 60.00 | 28.00 |
| 016B (40/3) | 0.79 | 0.48 | 40.34 | 60.00 | 32.00 |
| 016C (40/6) | 0.83 | 0.62 | 40.22 | 60.00 | 30.00 |

[1]Temperature (° C.)/time (months);
[2]Disintegration test according to USP current edition.

The data in Table 5 shows that, for the tablets with film-coated acidic cores with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 6

Shelf life of Batch 029-40 mg sodium pantoprazole tablets (quali/quantitative composition of Example 3)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 029 (20/0) | 0.45 | 0.65 | 40.00 | 60.00 | 24.00 |
| 029A (25/3) | 0.67 | 0.44 | 40.42 | 60.00 | 25.00 |
| 029B (25/6) | 0.72 | 0.58 | 39.94 | 60.00 | 28.00 |
| 029C (25/12) | 0.88 | 0.68 | 39.72 | 60.00 | 28.00 |

[1]Temperature (° C.)/time (months);
[2]Disintegration test according to USP current edition.

Example 4: 40.0 mg Gastroresistant Sodium Pantoprazole Tablets without Sodium Starch Glycolate

| | |
|---|---|
| A. Sodium pantoprazole | 40.00 mg |
| C. Maltodextrine | 70.00 mg |
| D. Mannitol | 50.00 mg |
| E. Calcium sulphate dihydrate | 40.00 mg |
| F. Calcium phosphate dihydrate | 40.00 mg |
| G. Magnesium stearate | 20.00 mg |
| H. Malic acid | 80.00 mg |
| I. Stearic acid | 40.00 mg |
| Total core weight | 380.00 mg |
| L. Arginine Shellac | 30.00 mg |
| M. Titanium dioxide | 5.00 mg |
| N. Talc | 10.00 mg |
| O. Triethyl citrate | 5.00 mg |
| P. Precipitated silica | 2.00 mg |
| Q. Yellow tartrazine | 0.050 mg |
| Total tablet weight | 432.05 mg |

TABLE 7

Stress test of Batches 004 and 017-40 mg sodium pantoprazole tablets without disintegrant (quali/quantitative composition of Example 4)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 004 (20/0) | 0.44 | 0.54 | 40.63 | 60.00 | 45.00 |
| 004A (40/1) | 0.65 | 0.32 | 39.35 | 60.00 | 56.00 |
| 004B (40/3) | 0.59 | 0.56 | 41.04 | 60.00 | 65.00 |
| 004C (40/6) | 0.76 | 0.63 | 39.71 | 60.00 | 68.00 |
| 017 (20/0) | 0.39 | 0.65 | 41.33 | 60.00 | 50.00 |
| 017A (40/1) | 0.58 | 0.55 | 40.00 | 60.00 | 62.00 |
| 017B (40/3) | 0.53 | 0.62 | 40.24 | 60.00 | 68.00 |
| 017C (40/6) | 0.64 | 0.68 | 39.00 | 60.00 | 76.00 |

[1]Temperature (° C.)/time (months);
[2]Disintegration test according to USP current edition.

The data in Table 7 shows that, for tablets with acidic film-coated cores without the presence of sodium starch glycolate in the coating film, they have considerably longer disintegration times at pH 6.8 (according to USP current edition) at time zero, and the variation thereof again at pH 6.8 is not constant over time after the samples have been conserved at 40° C. for 6 months.

TABLE 8

Shelf life of Batch 030-40 mg sodium pantoprazole tablets (quali/quantitative composition of Example 4)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 030 (20/0) | 0.46 | 0.52 | 41.09 | 60.00 | 52.00 |
| 030A (25/3) | 0.44 | 0.44 | 40.75 | 60.00 | 57.00 |
| 030B (25/6) | 0.65 | 0.61 | 40.74 | 60.00 | 58.00 |
| 030C (25/12) | 0.69 | 0.63 | 39.69 | 60.00 | 69.00 |

[1]Temperature (° C.)/time (months);
[2]Disintegration test according to USP current edition.

Example 5: 40.0 mg Gastroresistant Sodium Pantoprazole Tablets with Crospovidone (Kollidon CL)

| | |
|---|---|
| A. Sodium pantoprazole | 40.00 mg |
| C. Maltodextrine | 70.00 mg |
| D. Mannitol | 50.00 mg |
| E. Calcium sulphate dehydrate | 40.00 mg |
| F. Calcium phosphate dihydrate | 40.00 mg |
| G. Magnesium stearate | 20.00 mg |
| H. Malic acid | 80.00 mg |
| I. Stearic acid | 40.00 mg |
| Total core weight | 380.00 mg |
| L. Arginine Shellac | 30.00 mg |
| M. Crospovidone (Kollidon CL) | 6.0 mg |
| N. Titanium dioxide | 5.00 mg |
| O. Talc | 10.00 mg |
| P. Triethyl citrate | 5.00 mg |
| Q. Precipitated silica | 2.00 mg |
| R. Yellow tartrazine | 0.050 mg |
| Total tablet weight | 438.05 mg |

TABLE 9

Stress test of Batches 005 and 018-40 mg sodium pantoprazole tablets with Crospovidone as disintegrant (quali/quantitative composition of Example 5)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 005 (20/0) | 0.65 | 0.49 | 41.54 | 34.00 | — |
| 005A (40/1) | 0.55 | 0.37 | 40.76 | 45.00 | — |
| 005B (40/3) | 0.53 | 0.46 | 40.14 | 37.00 | — |
| 005C (40/6) | 0.69 | 0.58 | 40.51 | 29.00 | — |
| 018 (20/0) | 0.58 | 0.52 | 40.43 | 42.00 | — |
| 018A (40/1) | 0.53 | 0.67 | 40.78 | 55.00 | — |
| 018B (40/3) | 0.69 | 0.61 | 39.98 | 47.00 | — |
| 018C (40/6) | 0.71 | 0.64 | 40.11 | 49.00 | — |

[1]Temperature (° C.)/time (months);
[2]Disintegration test according to USP current edition.

The data in Table 9 shows that the acidic film-coated tablets in the presence of Crospovidone (Kollidon CL) in the coating film replacing the sodium starch glycolate as another superdisintegrant, do not pass the acid resistance test of at least one hour in an acidic environment at pH 1.2 according to USP current edition. Indeed, the disintegration test at pH 6.8 is cancelled.

TABLE 10

Shelf life of Batch 031-40 mg sodium pantoprazole tablets (quali/quantitative composition of Example 5)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 031 (20/0) | 0.34 | 0.44 | 39.87 | 32.00 | — |
| 031A (25/3) | 0.45 | 0.66 | 40.32 | 43.00 | — |
| 031B (25/6) | 0.53 | 0.72 | 39.99 | 45.00 | — |
| 031C (25/12) | 0.67 | 0.66 | 39.71 | 41.00 | — |

[1]Temperature (° C.)/time (months);
[2]Disintegration test according to USP current edition.

Example 6: 200 mg Gastroresistant Ibuprofen Tablets

| | |
|---|---|
| A. Ibuprofen | 200.00 mg |
| B Magnesium oxide | 70.00 mg |
| C. Magnesium hydroxide | 100.00 mg |
| D. Xylitol | 50.00 mg |
| E. Calcium carbonate | 100.00 mg |
| F. Microcrystalline cellulose | 60.00 mg |
| G. Magnesium stearate | 20.00 mg |
| H. Stearic acid | 40.00 mg |
| Total core weight | 570.00 mg |
| I. Arginine Shellac | 30.00 mg |
| L. Sodium starch glycolate | 6.0 mg |
| M. Titanium dioxide | 5.00 mg |
| N. Talc | 10.00 mg |
| O. Triethyl citrate | 5.00 mg |
| P. Precipitated silica | 2.00 mg |
| Q. Yellow tartrazine | 0.050 mg |
| Total tablet weight | 628.05 mg |

The cores, due to the presence of oxides and carbonate, are characterised by having a basic pH, so as to test the behaviour of the film on this type of cores.

TABLE 11

Stress test of Batches 006 and 019-200 mg ibuprofen tablets (quali/quantitative composition of Example 6)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 006 (20/0) | 0.78 | 0.76 | 210.24 | 60.00 | 25.00 |
| 006A (40/1) | 0.87 | 0.87 | 211.22 | 60.00 | 24.00 |
| 006B (40/3) | 0.98 | 0.96 | 209.21 | 60.00 | 27.00 |
| 006C (40/6) | 0.99 | 0.88 | 208.99 | 60.00 | 24.00 |
| 019 (20/0) | 0.67 | 0.88 | 208.09 | 60.00 | 24.00 |
| 019A (40/1) | 0.76 | 1.09 | 207.34 | 60.00 | 24.00 |
| 019B (40/3) | 0.86 | 0.96 | 206.71 | 60.00 | 26.00 |
| 019C (40/6) | 0.87 | 1.08 | 207.12 | 60.00 | 27.00 |

[1]Temperature (° C.)/time (months);
[2]Disintegration test according to USP current edition.

The data in Table 11 shows that in tablets with base film-coated cores with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 12

Shelf life of Batch 032-200 mg ibuprofen tablets (quali/quantitative composition of Example 6)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 032 (20/0) | 0.54 | 0.76 | 209.19 | 60.00 | 25.00 |
| 032A (25/3) | 0.66 | 1.00 | 208.36 | 60.00 | 29.00 |
| 032B (25/6) | 0.73 | 0.94 | 207.95 | 60.00 | 29.00 |
| 032C (25/12) | 0.79 | 1.12 | 206.42 | 60.00 | 34.00 |

[1]Temperature (° C.)/time (months);
[2]Disintegration test according to USP current edition.

Example 7: 200 mg Gastroresistant Ibuprofen Tablets without Sodium Starch Glycolate

| | | |
|---|---|---|
| A. Ibuprofen | 200.00 | mg |
| B. Magnesium oxide | 70.00 | mg |
| C. Magnesium hydroxide | 100.00 | mg |
| D. Xylitol | 50.00 | mg |
| E. Calcium carbonate | 100.00 | mg |
| F. Microcrystalline cellulose | 60.00 | mg |
| G. Magnesium stearate | 20.00 | mg |
| H. Stearic acid | 40.00 | mg |
| Total core weight | 570.00 | mg |
| I. Arginine Shellac | 30.00 | mg |
| L. Titanium dioxide | 5.00 | mg |
| M. Talc | 10.00 | mg |
| N. Triethyl citrate | 5.00 | mg |
| O. Precipitated silica | 2.00 | mg |
| P. Yellow tartrazine | 0.050 | mg |
| Total tablet weight | 622.05 | mg |

TABLE 13

Stress test of Batches 007 and 020-200 mg ibuprofen tablets (quali/quantitative composition of Example 7)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 007 (20/0) | 0.65 | 0.54 | 211.34 | 60.00 | 48.00 |
| 007A (40/1) | 0.85 | 0.78 | 209.54 | 60.00 | 57.00 |
| 007B (40/3) | 0.89 | 0.87 | 208.27 | 60.00 | 66.00 |
| 007C (40/6) | 0.88 | 0.78 | 209.19 | 60.00 | 73.00 |
| 020 (20/0) | 0.54 | 0.65 | 208.34 | 60.00 | 52.00 |
| 020A (40/1) | 0.76 | 0.68 | 207.11 | 60.00 | 62.00 |
| 020B (40/3) | 0.79 | 0.78 | 207.00 | 60.00 | 73.00 |
| 020C (40/6) | 0.82 | 0.82 | 206.02 | 60.00 | 78.00 |

[1]Temperature (° C.)/time (months);
[2]Disintegration test according to USP current edition.

The data in Table 13 shows that tablets with base film-coated cores without the presence of sodium starch glycolate in the coating film have considerably longer disintegration times at pH 6.8 (according to USP current edition) at time zero, and the variation thereof again at pH 6.8 is not constant over time after the samples have been conserved at 40° C. for 6 months.

TABLE 14

Shelf life of Batch 033-200 mg ibuprofen tablets (quali/quantitative composition of example 7)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 033 (20/0) | 0.79 | 0.59 | 208.00 | 60.00 | 50.00 |
| 033A (25/3) | 0.72 | 0.76 | 207.87 | 60.00 | 54.00 |
| 033B (25/6) | 0.89 | 0.72 | 207.32 | 60.00 | 63.00 |
| 033C (25/12) | 0.98 | 0.89 | 206.99 | 60.00 | 68.00 |

[1]Temperature (° C.)/time (months);
[2]Disintegration test according to USP current edition.

Example 8: 1000 mg Gastroresistant Lactic Ferments Tablets

| | | |
|---|---|---|
| A. Lactic ferments | 1000.00 | mg |
| B Microcrystalline cellulose | 70.00 | mg |
| C. Glycerol behenate | 100.00 | mg |
| D. calcium phosphate dihydrate | 150.00 | mg |
| E. Magnesium stearate | 20.00 | mg |
| F. Stearic acid | 40.00 | mg |
| G. Hydrogenated fatty acid | 40.00 | mg |
| Total core weight | 1420.00 | mg |
| H. Arginine Shellac | 30.00 | mg |
| I. Sodium starch glycolate | 6.0 | mg |
| L. Titanium dioxide | 5.00 | mg |
| M. Talc | 10.00 | mg |
| N. Triethyl citrate | 5.00 | mg |
| O. Precipitated silica | 2.00 | mg |
| P. Yellow tartrazine | 0.050 | mg |
| Total tablet weight | 1478.05 | mg |

TABLE 15

Stress test of Batches 008 and 021-1000 mg lactic ferments tablets (quali/quantitative composition of Example 8)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 008 (20/0) | 0.35 | 3.54 | 5.00 ml | 60.00 | 28.00 |
| 008A (40/1) | 0.23 | 12.78 | 2.00 ml | 60.00 | 27.00 |
| 008B (40/3) | 0.19 | 24.87 | 0.5 ml | 60.00 | 26.00 |
| 008C (40/6) | 0.18 | 35.78 | 0.1 ml | 60.00 | 29.00 |
| 021 (20/0) | 0.40 | 3.21 | 5.60 ml | 60.00 | 30.00 |
| 021A (40/1) | 0.37 | 14.09 | 2.30 ml | 60.00 | 24.00 |
| 021B (40/3) | 0.39 | 25.98 | 0.73 ml | 60.00 | 27.00 |
| 021C (40/6) | 0.42 | 37.45 | 0.23 ml | 60.00 | 32.00 |

[1]Temperature (° C.)/time (months);
[2]Disintegration test according to USP current edition.

The data in Table 15 shows that, for film-coated lactic ferments tablets with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 16

Shelf life of Batch 034-1000 mg lactic ferments tablets (quali/quantitative composition of Example 8)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 034 (20/0) | 0.36 | 4.67 | 5.80 ml | 60.00 | 29.00 |
| 034A (25/3) | 0.65 | 6.45 | 4.80 ml | 60.00 | 28.00 |
| 034B (25/6) | 0.46 | 7.76 | 3.90 ml | 60.00 | 32.00 |
| 034C (25/12) | 0.59 | 13.03 | 3.60 ml | 60.00 | 33.00 |

[1]Temperature (° C.)/time (months);
[2]Disintegration test according to USP current edition.

Example 9: 1000 mg Gastroresistant Lactic Ferments Tablets without Sodium Starch Glycolate

| | |
|---|---|
| A. Live lactic ferments | 1000.00 mg |
| B Microcrystalline cellulose | 70.00 mg |
| C. Glycerol behenate | 100.00 mg |
| D. calcium phosphate dihydrate | 150.00 mg |
| E. Magnesium stearate | 20.00 mg |
| F. Stearic acid | 40.00 mg |
| G. Hydrogenated fatty acid | 40.00 mg |
| Total core weight | 1420.00 mg |
| H. Arginine Shellac | 30.00 mg |
| I. Titanium dioxide | 5.00 mg |
| L. Talc | 10.00 mg |
| M. Triethyl citrate | 5.00 mg |
| N. Precipitated silica | 2.00 mg |
| O. Yellow tartrazine | 0.050 mg |
| Total tablet weight | 1518.05 mg |

TABLE 17

Stress test of Batches 009 and 022-1000 mg lactic ferments tablets without sodium starch glycolate (quali/quantitative composition of Example 9)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 009 (20/0) | 0.43 | 3.78 | 5.00 ml | 60.00 | 38.00 |
| 009A (40/1) | 0.33 | 15.78 | 2.30 ml | 60.00 | 48.00 |
| 009B (40/3) | 0.34 | 27.17 | 0.6 ml | 60.00 | 56.00 |
| 009C (40/6) | 0.22 | 37.79 | 0.2 ml | 60.00 | 69.00 |
| 022 (20/0) | 0.56 | 4.89 | 5.50 ml | 60.00 | 45.00 |
| 022A (40/1) | 0.49 | 15.81 | 2.98 ml | 60.00 | 58.00 |
| 022B (40/3) | 0.52 | 30.56 | 0.78 ml | 60.00 | 69.00 |
| 022C (40/6) | 0.44 | 40.52 | 0.45 ml | 60.00 | 76.00 |

[1]Temperature (° C.)/time (months);
[2]Disintegration test according to USP current edition.

The data in Table 17 shows that film-coated lactic ferments tablets without the presence of sodium starch glycolate in the film have considerably longer disintegration times at pH 6.8 (according to USP current edition) at time zero, and the variation thereof again at pH 6.8 is not constant over time after the samples have been conserved at 40° C. for 6 months.

TABLE 18

Shelf life of Batch 035-1000 mg lactic ferments tablets without sodium starch glycolate (quali/quantitative composition of Example 9)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 035 (20/0) | 0.45 | 4.34 | 5.50 ml | 60.00 | 46.00 |
| 035A (25/3) | 0.43 | 7.23 | 4.98 ml | 60.00 | 48.00 |
| 035B (25/6) | 0.62 | 9.45 | 4.29 ml | 60.00 | 59.00 |
| 035C (25/12) | 0.63 | 14.23 | 3.75 ml | 60.00 | 64.00 |

[1]Temperature (° C.)/time (months);
[2]Disintegration test according to USP current edition.

Example 10: 11.0 mg Per Tablet Gastroresistant NADH Tablet

| DESCRIPTION OF THE COMPONENTS | | AMOUNT PER TABLET |
|---|---|---|
| Active ingredient | | |
| A) NADH | mg | 11.00 |
| B) Microcrystalline cellulose | mg | 7.00 |
| C) Sorbitol | mg | 26.0 |
| D) Glycerol behenate | mg | 2.00 |
| E) Magnesium oxide | mg | 8.0 |
| F) Magnesium stearate | mg | 0.50 |
| G) Calcium carbonate | mg | 1.00 |
| Weight of the core | mg | 55.50 |
| H) Arginine schellac | mg | 2.00 |
| I) Sodium starch glycolate | mg | 0.20 |
| L) Titanium dioxide | mg | 0.10 |
| M) Colloidal silica, anhydrous | mg | 0.20 |
| N) Talc | mg | 0.20 |
| O) Triethyl citrate | mg | 0.15 |
| Overall weight of the coated tablets | mg | 58.35 |

TABLE 19

Stress test of Batches 010 and 023-11.0 mg NADH tablets (quali/quantitative composition of Example 10)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 010 (20/0) | 3.40 | 1.41 | 10.43 | 60.00 | 28.00 |
| 010A (40/1) | 3.19 | 2.03 | 10.98 | 60.00 | 28.00 |
| 010B (40/3) | 3.44 | 2.43 | 9.21 | 60.00 | 26.00 |
| 010C (40/6) | 2.93 | 3.61 | 9.21 | 60.00 | 29.00 |
| 023 (20/0) | 3.89 | 1.09 | 10.87 | 60.00 | 23.00 |
| 023A (40/1) | 4.19 | 1.93 | 9.98 | 60.00 | 25.00 |
| 023B (40/3) | 3.87 | 2.04 | 9.00 | 60.00 | 29.00 |
| 023C (40/6) | 3.91 | 3.32 | 8.95 | 60.00 | 28.00 |

[1]Temperature (° C.)/time (months);
[2]Disintegration test according to USP current edition;

The data in Table 19 shows that, for 11 mg film-coated NADH tablets with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 20

Shelf life of Batch 036-11.0 mg NADH tablets (quali/quantitative composition of Example 10)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 036 (20/0) | 3.65 | 1.65 | 10.47 | 60.00 | 26.00 |
| 036A (25/3) | 4.57 | 2.09 | 10.08 | 60.00 | 29.00 |
| 036B (25/6) | 4.77 | 2.14 | 9.89 | 60.00 | 29.00 |
| 036C (25/12) | 4.21 | 2.67 | 8.56 | 60.00 | 30.00 |

[1]Temperature (° C.)/time (months);
[2]Disintegration test according to USP current edition.

Example 11: 5.5 mg Gastroresistant NADH Tablets

| DESCRIPTION OF THE COMPONENTS | | AMOUNT PER CPR |
|---|---|---|
| Active ingredient | | |
| A) NADH | Mg | 5.50 |
| B) Microcrystalline cellulose | Mg | 7.00 |
| C) Sorbitol | Mg | 20.0 |
| D) Glycerol behenate | Mg | 2.00 |
| E) Magnesium oxide | Mg | 14.00 |
| F) Magnesium stearate | Mg | 0.50 |
| G) Calcium carbonate | Mg | 1.00 |
| Weight of the core | Mg | 50.00 |
| H) Arginine schellac | Mg | 2.00 |
| I) Sodium starch glycolate | Mg | 0.20 |
| L) Titanium dioxide | Mg | 0.10 |
| M) Colloidal silica, anhydrous | Mg | 0.20 |
| N) Talc | mg | 0.20 |
| O) Triethyl citrate | mg | 0.15 |
| Overall weight of the coated tablets | mg | 52.85 |

TABLE 21

Stress test of Batches 011 and 024-5.5 mg NADH tablets (quali/quantitative composition of Example 11)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 011 (20/0) | 3.77 | 2.11 | 5.43 | 60.00 | 32.00 |
| 011A (40/1) | 4.19 | 2.53 | 5.18 | 60.00 | 34.00 |
| 011B (40/3) | 4.34 | 2.99 | 4.56 | 60.00 | 29.00 |
| 011C (40/6) | 3.99 | 3.91 | 4.06 | 60.00 | 31.00 |
| 024 20/0) | 3.43 | 2.43 | 5.32 | 60.00 | 30.00 |
| 024A (40/1) | 4.78 | 2.87 | 4.98 | 60.00 | 31.00 |
| 024B (40/3) | 6.09 | 3.43 | 4.32 | 60.00 | 27.00 |
| 024C (40/6) | 5.32 | 3.76 | 4.26 | 60.00 | 32.00 |

[1]Temperature (° C.)/time (months);
[2]Disintegration test according to USP current edition;

The data in Table 21 shows that, for film-coated NADH tablets of different dosage to 5.5 mg with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 22

Shelf life of Batch 037 5.5 mg NADH tablets (quali/quantitative composition of Example 11)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 037 (20/0) | 3.87 | 2.09 | 5.12 | 60.00 | 31.00 |
| 037A (25/3) | 3.99 | 2.03 | 5.00 | 60.00 | 35.00 |
| 037B (25/6) | 4.11 | 2.67 | 4.78 | 60.00 | 29.00 |
| 037C (25/12) | 4.89 | 2.98 | 4.66 | 60.00 | 33.00 |

[1]Temperature (° C.)/time (months);
[2]Disintegration test according to USP current edition.

Example 12: 11.0 mg/Tablet Gastroresistant NADH Tablets

| DESCRIPTION OF THE COMPONENTS | | AMOUNT PER TABLET |
|---|---|---|
| Active ingredient | | |
| A) NADH | mg | 11.00 |
| B) Microcrystalline cellulose | mg | 7.00 |
| C) Sorbitol | mg | 26.0 |
| D) Glycerol behenate | mg | 2.00 |
| E) Magnesium oxide | mg | 8.0 |
| F) Magnesium stearate | mg | 0.50 |
| G) Calcium carbonate | mg | 1.00 |
| Weight of the core | mg | 55.50 |
| H) Arginine schellac | mg | 2.00 |
| I) Titanium dioxide | mg | 0.10 |
| L) Colloidal silica, anhydrous | mg | 0.20 |
| M) Talc | mg | 0.20 |
| N) Triethyl citrate | mg | 0.15 |
| Overall weight of the coated tablets | mg | 58.35 |

TABLE 23

Stress test of Batches 012 and 025-11.0 mg NADH tablets without sodium starch glycolate (quali/quantitative composition of Example 12)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 012 (20/0) | 3.89 | 1.71 | 10.78 | 60.00 | 43.00 |
| 012A (40/1) | 3.90 | 2.53 | 10.12 | 60.00 | 47.00 |
| 012B (40/3) | 4.21 | 2.87 | 9.45 | 60.00 | 59.00 |
| 012C (40/6) | 3.93 | 3.89 | 9.09 | 60.00 | 67.00 |
| 025 (20/0) | 4.42 | 1.21 | 10.28 | 60.00 | 49.00 |
| 025A (40/1) | 4.23 | 2.98 | 10.00 | 60.00 | 53.00 |
| 025B (40/3) | 4.76 | 3.56 | 9.21 | 60.00 | 66.00 |
| 025C (40/6) | 4.02 | 4.82 | 9.00 | 60.00 | 72.00 |

[1]Temperature (° C.)/time (months);
[2]Disintegration test according to USP current edition;

The data in Table 23 shows that 11 mg film-coated NADH tablets without the presence of sodium starch glycolate in the film have considerably longer disintegration times at pH 6.8 (according to USP current edition) at time zero, and the variation thereof again at pH 6.8 is not constant over time after the samples have been conserved at 40° C. for 6 months.

TABLE 24

Shelf life of Batch 038 11.0 mg NADH tablets without sodium starch glycolate (quali/quantitative composition of Example 12)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 038 (20/0) | 3.93 | 1.11 | 10.13 | 60.00 | 45.00 |
| 038A (25/3) | 4.03 | 2.18 | 10.01 | 60.00 | 49.00 |
| 038B (25/6) | 4.45 | 2.53 | 9.71 | 60.00 | 56.00 |
| 038C (25/12) | 4.92 | 2.84 | 9.54 | 60.00 | 62.00 |

[1]Temperature (° C.)/time (months);
[2]Disintegration test according to USP current edition.

Example 13: 5.5 mg Gastroresistant NADH Tablets

| DESCRIPTION OF THE COMPONENTS | | AMOUNT PER TABLET |
|---|---|---|
| Active ingredient | | |
| A) NADH | mg | 5.50 |
| B) Microcrystalline cellulose | mg | 7.00 |
| C) Sorbitol | mg | 20.0 |
| D) Glycerol behenate | mg | 2.00 |
| E) Magnesium oxide | mg | 14.00 |
| F) Magnesium stearate | mg | 0.50 |
| G) Calcium carbonate | mg | 1.00 |
| Weight of the core | mg | 50.00 |
| H) Arginine schellac | mg | 2.00 |
| I) Titanium dioxide | mg | 0.10 |
| L) Colloidal silica, anhydrous | mg | 0.20 |
| M) Talc | mg | 0.20 |
| N) Triethyl citrate | mg | 0.15 |
| Overall weight of the coated tablets | mg | 52.85 |

TABLE 25

Stress test of Batches 013 and 026- 5.5 mg NADH tablets without sodium starch glycolate (quali/quantitative composition of Example 13)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 013 (20/0) | 3.97 | 2.00 | 5.13 | 60.00 | 42.00 |
| 013A (40/1) | 4.01 | 2.33 | 5.48 | 60.00 | 54.00 |
| 013B (40/3) | 4.24 | 2.59 | 4.34 | 60.00 | 69.00 |
| 013C (40/6) | 3.66 | 3.81 | 4.16 | 60.00 | 71.00 |
| 026 (20/0) | 4.54 | 2.54 | 5.32 | 60.00 | 51.00 |
| 026A (40/1) | 4.32 | 3.65 | 4.99 | 60.00 | 62.00 |
| 026B (40/3) | 4.67 | 3.09 | 4.54 | 60.00 | 71.00 |
| 026C (40/6) | 5.17 | 3.41 | 4.08 | 60.00 | 78.00 |

[1]Temperature (° C.)/time (months);
[2]Disintegration test according to USP current edition;

The data in Table 25 shows that 5.5 mg film-coated NADH tablets without the presence of sodium starch glycolate in the film, have considerably longer disintegration times at pH 6.8 (according to USP current edition) at time zero, and the variation thereof again at pH 6.8 is not constant over time after the samples have been conserved at 40° C. for 6 months.

TABLE 26

Shelf life of Batch 039- 5.5 mg NADH tablets without sodium starch glycolate (quali/quantitative composition of Example 13)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 039 (20/0) | 3.98 | 1.94 | 5.19 | 60.00 | 50.00 |
| 039A (25/3) | 4.62 | 2.45 | 5.34 | 60.00 | 57.00 |
| 039B (25/6) | 4.27 | 2.89 | 4.84 | 60.00 | 60.00 |
| 039C (25/12) | 4.89 | 3.05 | 4.68 | 60.00 | 64.00 |

[1]Temperature (° C.)/time (months);
[2]Disintegration test according to USP current edition.

From the stability data at 40° C. and 75% R.H. (stress test) and from the stability data at 25° C. and 60% R.H. (shelf life) it is possible to observe that all of the batches examined having sodium starch glycolate in the coating film have considerably shorter disintegration times at time zero with respect to those without sodium starch glycolate.

After six months the samples with sodium starch glycolate had not undergone a difference in the disintegration test evaluated as disintegration time at pH 6.8. On the other hand, after six months the samples without sodium starch glycolate had undergone a substantial difference in the disintegration test evaluated as disintegration time at pH 6.8.

The sample with a different superdisintegrant does not pass the test at acidic pH due to the different behaviour that is has with respect to sodium starch glycolate.

Moreover, from the stability at 25° C. and 60% R.H. (shelf life) it can be observed that after twelve months the samples with sodium starch glycolate had not undergone a difference in the disintegration test evaluated as disintegration time at pH 6.8, whereas on the other hand after twelve months the samples without sodium starch glycolate had undergone a substantial difference in the disintegration test evaluated as disintegration time at pH 6.8.

The sample with a different superdisintegrant does not pass the test at acidic pH due to the different behaviour that it has with respect to sodium starch glycolate.

Example 14: 200 mg Gastroresistant Ibuprofen Type 0 Capsules

| A. Ibuprofen | 200.00 mg |
|---|---|
| B Mannitol | 70.00 mg |
| C. Maltodextrine | 100.00 mg |
| D. Xylitol | 50.00 mg |
| E. Microcrystalline cellulose | 60.00 mg |
| F. Magnesium stearate | 20.00 mg |
| G. Stearic acid | 40.00 mg |
| Total core weight | 470.00 mg |
| H. Arginine Shellac | 30.00 mg |
| I. Sodium starch glycolate | 6.0 mg |
| L. Titanium dioxide | 5.00 mg |
| M. Talc | 10.00 mg |
| N. Triethyl citrate | 5.00 mg |
| O. Precipitated silica | 2.00 mg |
| P. Yellow tartrazine | 0.050 mg |
| Total tablet weight | 528.05 mg |

TABLE 27

Stress test of Batches 040 and 041- 200 mg ibuprofen capsules (quali/quantitative composition of Example 14)

| Batch (T/t)[1] | Humidity % (K.F.) | Total impurities | Amount mg/cpr | Resistance to gastric juice at pH 1.2[2] (minutes) | Disintegration time at pH 6.8[2] (minutes) |
|---|---|---|---|---|---|
| 040 (20/0)   | 0.34 | 0.88 | 209.56 | 60.00 | 29.00 |
| 040A (40/1)  | 0.43 | 0.98 | 209.00 | 60.00 | 27.00 |
| 040B (40/3)  | 0.54 | 0.93 | 208.92 | 60.00 | 28.00 |
| 040C (40/6)  | 0.65 | 0.76 | 208.69 | 60.00 | 28.00 |
| 041 (20/0)   | 0.44 | 0.70 | 208.99 | 60.00 | 29.00 |
| 041A (40/1)  | 0.55 | 0.99 | 208.94 | 60.00 | 28.00 |
| 041B (40/3)  | 0.51 | 0.95 | 209.32 | 60.00 | 29.00 |
| 041C (40/6)  | 0.49 | 0.88 | 208.82 | 60.00 | 30.00 |

[1]Temperature (° C.)/time (months);
[2]Disintegration test according to USP current edition.

The data in Table 27 shows that in capsules with films with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 28

Shelf life of Batch 042- 200 mg ibuprofen capsules (quali/quantitative composition of Example 14)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 042 (20/0)  | 0.66 | 0.88 | 208.68 | 60.00 | 29.00 |
| 042A (25/3) | 0.73 | 1.12 | 208.96 | 60.00 | 24.00 |
| 042B (25/6) | 0.62 | 0.98 | 208.21 | 60.00 | 26.00 |
| 042C (25/12)| 0.59 | 1.09 | 207.92 | 60.00 | 32.00 |

[1]Temperature (° C.)/time (months);
[2]Disintegration test according to USP current edition.

Example 15: 200 mg Gastroresistant Ibuprofen Capsules without Sodium Starch Glycolate

| | |
|---|---|
| A. Ibuprofen | 200.00 mg |
| B. Mannitol | 70.00 mg |
| C. Maltodextrine | 100.00 mg |
| D. Xylitol | 50.00 mg |
| E. Microcrystalline cellulose | 60.00 mg |
| F. Magnesium stearate | 20.00 mg |
| G. Stearic acid | 40.00 mg |
| Total core weight | 470.00 mg |
| H. Arginine Shellac | 30.00 mg |
| I. Titanium dioxide | 5.00 mg |
| L. Talc | 10.00 mg |
| M. Triethyl citrate | 5.00 mg |
| N. Precipitated silica | 2.00 mg |
| O. Yellow tartrazine | 0.050 mg |
| Total tablet weight | 522.05 mg |

TABLE 29

Stress test of Batches 043 and 044- 200 mg ibuprofen capsules (quali/quantitative composition of Example 15)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 043 (20/0)   | 0.49 | 0.34 | 210.54 | 60.00 | 49.00 |
| 043A (40/1)  | 0.43 | 0.33 | 209.98 | 60.00 | 58.00 |
| 043B (40/3)  | 0.55 | 0.45 | 209.87 | 60.00 | 73.00 |
| 043C (40/6)  | 0.36 | 0.68 | 208.87 | 60.00 | 83.00 |
| 044 (20/0)   | 0.65 | 0.43 | 209.67 | 60.00 | 59.00 |
| 044A (40/1)  | 0.43 | 0.44 | 209.13 | 60.00 | 72.00 |
| 044B (40/3)  | 0.34 | 0.54 | 209.07 | 60.00 | 78.00 |
| 044C (40/6)  | 0.23 | 0.62 | 208.32 | 60.00 | 88.00 |

[1]Temperature (° C.)/time (months);
[2]Disintegration test according to USP current edition.

The data in Table 29 shows that film-coated capsules without the presence of sodium starch glycolate in the coating film have considerably longer disintegration times at pH 6.8 (according to USP current edition) at time zero, and the variation thereof again at pH 6.8 is not constant over time after the samples have been conserved a 40° C. for 6 months.

TABLE 30

Shelf life of Batch 045- 200 mg ibuprofen capsules (quali/quantitative composition of Example 15)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 045 (20/0)  | 0.45 | 0.69 | 209.34 | 60.00 | 54.00 |
| 045A (25/3) | 0.44 | 0.56 | 209.02 | 60.00 | 57.00 |
| 045B (25/6) | 0.36 | 0.62 | 208.90 | 60.00 | 73.00 |
| 045C (25/12)| 0.28 | 0.78 | 208.99 | 60.00 | 88.00 |

[1]Temperature (° C.)/time (months);
[2]Disintegration test according to USP current edition.

Example 16: 400 mg IONE SAMe/Cpr Gastroresistant Tablets

| | |
|---|---|
| A. SAMe sulphate p-toluenesulfonate | 830.00 mg |
| B. Mannitol | 42.000 mg |
| C. Silica (Aerosil ®) | 2.00 mg |
| D. Anhydrous microcrystalline cellulose 112 | 114.00 mg |
| E. Vegetable magnesium stearate | 12.00 mg |
| Total core weight | 1000.00 mg |
| F. Arginine Shellac ® | 21.00 mg |
| G. Titanium dioxide | 2.62 mg |
| H. Talc | 7.87 mg |
| I. Triethyl citrate | 7.87 mg |
| L. Sodium starch glycolate (explotab) | 1.50 mg |
| M. Silica (Aerosil ®) | 2.62 mg |
| Total tablet weight | 1043.48 mg |

Production of the Cores:
1.1. Mixing

The work environment is conditioned to a temperature of 20° C. and to a relative humidity value equal to about 20% R.H. Then A, B, C, D, and E are transferred in the amounts indicated in Example 16 into the "Viani" biconical mixer leaving it under stirring for about 30 minutes. At the end of such an operation, the resulting mixture is transferred into dry recipients, still controlling humidity and temperature.

Then comes the direct compression of the mixture of powder through a rotary machine equipped with oblong punches of 19.0×8.8 mm adjusting the weight to 1050 mg/cpr and the compression force to about 35 KP. The tablets produced have a hardness of between 33 and 37 Kp.

Friability: ≤1.0%; disintegration time: ≤15 minutes (measured according to the method described in U.S.P. Current edition.)

Humidity according to K.F. ≤1.5%.

The stability tests on the uncoated cores were carried out just at 40° C. and 75% R.H for six months and for a single batch since they are not a finished product. The samples were conserved in capped and sealed glass flasks to simulate the final packaging (alu/alu blister pack).

TABLE 31

Batch 001- 400 mg uncoated ion/cpr cores (Example 16)

| Batch (T/t)[1] | Humidity % (K. Fischer) | Total impurities[2] (%) | SAMe[3] | S,S % |
|---|---|---|---|---|
| 001 (20/0) | 1.17 | 0.54 | 408.45 | 82.03 |
| 001A (40/1) | 1.28 | 0.67 | 406.97 | 78.12 |
| 001B (40/3) | 1.29 | 1.49 | 400.22 | 70.84 |
| 001C (40/6) | 1.33 | 2.58 | 399.54 | 66.12 |

[1]Temperature (° C.)/time (months);
[2]total impurities;
[3]SAMe sulphate p-toluenesulfonate (mg/cpr).

The tablets resulting from the previous processing steps were film-coated in a coating pan.

TABLE 32

Stress test of Batches 002 and 003 - 400 mg SAMe sulphate p-toluenesulfonate tablets (quali/quantitative composition of Example 16)

| Batch (T/t)[1] | Humidity % (K.F.) | Total impurities | S,S % | Count mg/cpr | Resistance to gastric juice at pH 1.2[2] (minutes) | Disintegration time at pH 6.8[2] (minutes) |
|---|---|---|---|---|---|---|
| 002 (20/0) | 1.24 | 0.62 | 83.14 | 408.45 | 60.00 | 27.00 |
| 002A (40/1) | 1.25 | 0.59 | 80.21 | 406.40 | 60.00 | 26.00 |
| 002B (40/3) | 1.13 | 0.99 | 75.23 | 404.12 | 60.00 | 29.00 |
| 002C (40/6) | 1.12 | 1.69 | 70.21 | 403.00 | 60.00 | 29.00 |
| 003 (20/0) | 1.22 | 0.63 | 82.33 | 409.23 | 60.00 | 27.00 |
| 003A (40/1) | 1.13 | 0.92 | 79.21 | 407.67 | 60.00 | 28.00 |
| 003B (40/3) | 1.11 | 1.22 | 76.32 | 406.32 | 60.00 | 29.00 |
| 003C (40/6) | 1.22 | 1.88 | 69.25 | 404.56 | 60.00 | 30.00 |

[1]Temperature (° C.)/time (months);
[2]Disintegration test according to USP current edition.

TABLE 33

Shelf life of Batch 004- 400 mg SAMe sulphate p-toluenesulfonate tablets (quali/quantitative composition of Example 16)

| Batch (T/t)1 | Humidity % (K.F.) | Total impurities | S,S | Count mg/cpr | Resistance to gastric juice at pH 1.22 (minutes) | Disintegration time at pH 6.82 (minutes) |
|---|---|---|---|---|---|---|
| 004 (20/0) | 1.21 | 0.53 | 82.16 | 408.37 | 60.00 | 30.00 |
| 004A (25/3) | 1.23 | 0.64 | 81.92 | 408.14 | 60.00 | 30.00 |
| 004B (25/6) | 1.46 | 0.62 | 81.63 | 407.12 | 60.00 | 29.00 |
| 004C (25/12) | 1.34 | 0.87 | 81.20 | 406.22 | 60.00 | 29.00 |

[1]Temperature (° C.)/time (months);
[2]Disintegration test according to USP current edition.

The data in Tables 32 and 33 shows that both the samples subjected to stress testing and those conserved at room temperature, in the presence of sodium starch glycolate in the coating film have disintegration times at pH 6.8 within specifications according to the disintegration test described in USP current edition and the variation of the disintegration again at pH 6.8 is constant over time.

The data in Tables 32 and 33 also shows that the samples of SAMe sulphate p-toluenesulfonate subjected both to stress testing and conserved at room temperature have a greater stability with respect to the cores of the same example before coating with the film described in the present invention.

Example 17: 400 mg TONE SAMe/Cpr Gastroresistant Tablets

| A. SAMe sulphate p-toluenesulfonate | 830.00 mg |
|---|---|
| B. Mannitol | 42.000 mg |
| C. Silica (Aerosil ®) | 2.00 mg |
| D. Anhydrous microcrystalline cellulose 112 | 114.00 mg |
| E. Vegetable magnesium stearate | 12.00 mg |
| Total core weight | 1000.00 mg |
| F. Arginine Shellac ® | 21.00 mg |
| G. Titanium dioxide | 2.62 mg |
| H. Talc | 7.87 mg |
| I. Triethyl citrate | 7.87 mg |
| L. Silica (Aerosil ®) | 2.62 mg |
| Total tablet weight | 1041.98 mg |

TABLE 34

Batch 005- 400 mg uncoated ion/cpr cores (Example 17)

| Batch (T/t)[1] | Humidity % (K. Fischer) | Total impurities[2] (%) | SAMe[3] | S,S % |
|---|---|---|---|---|
| 005 (20/0) | 1.37 | 0.46 | 408.45 | 82.33 |
| 005° (40/1) | 1.24 | 0.57 | 406.47 | 72.42 |
| 005B (40/3) | 1.41 | 1.75 | 404.25 | 67.11 |
| 005C (40/6) | 1.39 | 2.79 | 402.74 | 60.15 |

[1]Temperatura (° C.)/time (months);
[2]total impurities;
[3]SAMe sulphate p-toluenesulfonate (mg/cpr).

The tablets resulting from the processing steps like in Example 17 were film-coated in coating pan.

TABLE 35

Stress test of Batches 006 and 007 - 400 mg SAMe sulphate p-toluenesulfonate tablets (quali/quantitative composition of Example 17)

| Batch (T/t)[1] | Humidity % (K.F.) | Total impurities | S,S % | Count mg/cpr | Resistance to gastric juice at pH 1.2[2] (minutes) | Disintegration time at pH 6.8[2] (minutes) |
|---|---|---|---|---|---|---|
| 006 (20/0) | 1.43 | 0.55 | 83.34 | 408.90 | 60.00 | 29.00 |
| 006A (40/1) | 1.35 | 0.79 | 80.00 | 407.12 | 60.00 | 37.00 |
| 006B (40/3) | 1.33 | 0.89 | 72.53 | 403.89 | 60.00 | 40.00 |
| 006C (40/6) | 1.32 | 1.89 | 68.21 | 402.45 | 60.00 | 71.00 |
| 007 (20/0) | 1.42 | 0.53 | 82.11 | 408.54 | 60.00 | 39.00 |
| 007A (40/1) | 1.33 | 0.82 | 78.11 | 406.89 | 60.00 | 49.00 |
| 007B (40/3) | 1.43 | 1.02 | 74.92 | 405.21 | 60.00 | 59.00 |
| 007C (40/6) | 1.37 | 2.12 | 69.00 | 402.23 | 60.00 | 62.00 |

[1]Temperature (° C.)/time (months);
[2]Disintegration test according to USP current edition.

TABLE 36

Shelf life of Batch 008- 400 mg SAMe sulphate p-toluenesulfonate tablets (quali/quantitative composition of Example 17)

| Batch (T/t)1 | Humidity % (K.F.) | Total impurities | S,S % | Count mg/cpr | Resistance to gastric juice at pH 1.2[2] (minutes) | Disintegration time at pH 6.8[2] (minutes) |
|---|---|---|---|---|---|---|
| 008 (20/0) | 1.34 | 0.63 | 82.16 | 408.37 | 60.00 | 41.00 |
| 008A (25/3) | 1.54 | 0.60 | 80.92 | 407.56 | 60.00 | 51.00 |
| 008B (25/6) | 1.40 | 0.89 | 80.63 | 405.76 | 60.00 | 60.00 |
| 008C (25/12) | 1.34 | 0.97 | 78.67 | 405.98 | 60.00 | 71.00 |

1Temperature (° C.)/time (months);
[2]Disintegration test according to USP current edition.

The data in Tables 35 and 36 shows that both the samples subjected to stress testing and those conserved at room temperature, in the absence of sodium starch glycolate in the coating film, have disintegration times at pH 6.8 outside specifications according to the disintegration test described in USP current edition and the variation of the disintegration again at pH 6.8 is not constant over time.

The data in Tables 35 and 36 also shows that the samples of SAMe sulphate p-toluenesulfonate subjected both to stress testing and conserved at room temperature have a greater stability with respect to cores of the same example before coating with the film described in the present invention.

Example 18: 200 mg IONE SAMe/Cpr Gastroresistant Tablets

| | |
|---|---|
| A. SAMe sulphate p-toluenesulfonate | 415.40 mg |
| B. Anhydrous calcium chloride powder | 23.40 mg |
| C. Silica (Aerosil ®) | 2.00 mg |
| D. Anhydrous microcrystalline cellulose 112 | 151.00 mg |
| E. Vegetable magnesium stearate | 8.20 mg |
| Total core weight | 600.00 mg |
| F. Arginine Shellac ® | 14.00 mg |
| G. Titanium dioxide | 1.75 mg |
| H. Talc | 5.25 mg |
| I. Triethyl citrate | 5.25 mg |
| L. Sodium starch glycolate (explotab) | 1.00 mg |
| M. Silica (Aerosil ®) | 1.75 mg |
| Total tablet weight | 629.00 mg |

Production of the Cores: For the Process Refer to Example 16.

TABLE 37

Batch 009- 200 mg uncoated ion/cpr cores (Example 18)

| Batch (T/t)[1] | Humidity % (K. Fischer) | Total impurities[2] (%) | SAMe[3] | S,S % |
|---|---|---|---|---|
| 009 (20/0) | 132 | 0.45 | 204.21 | 84.55 |
| 009A (40/1) | 1.29 | 0.70 | 204.01 | 82.21 |
| 009B (40/3) | 1.35 | 1.51 | 202.32 | 78.32 |
| 009C (40/6) | 1.36 | 1.91 | 201.00 | 72.43 |

[1]Temperature (° C.)/time (months);
[2]total impurities;
[3]SAMe sulphate p-toluenesulfonate (mg/cpr);

The tablets resulting from the previous processing steps were film-coated in coating pan.

TABLE 38

Stress test of Batches 010 and 011 - 200 mg SAMe sulphate p-toluenesulfonate tablets (quali/quantitative composition of Example 18)

| Batch (T/t)1 | Humidity % (K.F.) | Total impurities | S,S % | Count mg/cpr | Resistance to gastric juice at pH 1.22 (minutes) | Disintegration time at pH 6.82 (minutes) |
|---|---|---|---|---|---|---|
| 010 (20/0) | 1.11 | 0.54 | 83.22 | 206.76 | 60.00 | 30.00 |
| 010A (40/1) | 1.33 | 0.78 | 81.19 | 205.64 | 60.00 | 29.00 |
| 010B (40/3) | 1.22 | 0.98 | 79.42 | 204.82 | 60.00 | 28.00 |
| 010C (40/6) | 1.54 | 1.23 | 77.34 | 203.99 | 60.00 | 29.00 |
| 011 (20/0) | 1.22 | 0.53 | 82.33 | 207.71 | 60.00 | 27.00 |
| 011A (40/1) | 1.23 | 0.69 | 81.67 | 206.19 | 60.00 | 29.00 |
| 011B (40/3) | 1.25 | 0.88 | 78.34 | 205.92 | 60.00 | 30.00 |
| 011C (40/6) | 1.12 | 1.28 | 77.24 | 204.98 | 60.00 | 29.00 |

1Temperature (° C.)/time (months);
2Disintegration test according to USP current edition.

TABLE 39

Shelf life of Batch 012- 200 mg SAMe sulphate p-toluenesulfonate tablets (quali/quantitative composition of Example 18)

| Batch (T/t)1 | Humidity % (K.F.) | Total impurities | S,S % | Count mg/cpr | Resistance to gastric juice at pH 1.2[2] (minutes) | Disintegration time at pH 6.8[2] (minutes) |
|---|---|---|---|---|---|---|
| 012 (20/0) | 1.39 | 0.57 | 83.00 | 206.89 | 60.00 | 30.00 |
| 012A (25/3) | 1.32 | 0.65 | 82.21 | 205.76 | 60.00 | 30.00 |
| 012B (25/6) | 1.28 | 082 | 78.39 | 204.00 | 60.00 | 27.00 |
| 012C (25/12) | 1.35 | 1.23 | 76.14 | 203.92 | 60.00 | 29.00 |

1Temperature (° C.)/time (months);
[2]Disintegration test according to USP current edition.

The data in Tables 38 and 39 shows that both the samples subjected to stress testing and those conserved at room temperature, in the presence of sodium starch glycolate in the coating film, have disintegration times at pH 6.8 within specifications according to the disintegration test described in USP current edition and the variation of the disintegration again at pH 6.8 is constant over time.

The data in Tables 38 and 39 also shows that the stability of SAMe sulphate p-toluenesulfonate on the samples subjected both to stress testing and conserved at room temperature have a greater stability with respect to cores of the same example before coating with the film described in the present invention.

Example 19: 30 Lansoprazole Capsules

| | |
|---|---|
| A. Lansoprazole | 30.00 mg |
| B Microcrystalline cellulose | 170.00 mg |
| C. Mannitol | 80.00 mg |
| D. Sorbitol | 150.00 mg |
| E. Silicon dioxide | 2.00 mg |
| F. Magnesium stearate | 2.00 mg |
| Net capsule weight | 434.00 mg |
| G. Arginine Shellac | 30.00 mg |
| H. Sodium starch glycolate | 6.0 mg |
| I. Titanium dioxide | 5.00 mg |
| L. Talc | 10.00 mg |
| M. Triethyl citrate | 5.00 mg |
| N. Precipitated silica | 2.00 mg |
| Total capsule weight (including capsule weight) | 692.00 mg |

1. Mixing

The work environment is conditioned to a temperature of 25° C. and to a relative humidity value equal to about 40% R.H. Then A, B, C, D, E, F, G and H are transferred in the amounts indicated above, into the mixer, leaving it under stirring for about 30 minutes. At the end of such an operation, the resulting mixture is transferred into dry recipients, again controlling humidity and temperature.

2. Incapsulation

There is then the final incapsulation of the mixture through a Zanasi rotary machine equipped with a pre-compression station and producing capsules with net weight of about 492 mg. The capsules produced have a weight of between 470 and 510 ng.

3. Film-Coating of the Capsules

In a recipient having suitable dimensions the shellac with arginine base is dissolved at 60° C., the sodium starch glycolate is added and it is brought to 80° C. until a solution is obtained with 20% p/v of arginine schellac salt with 4% sodium starch glycolate in suspension. Thereafter, under constant stirring, the glycerol is added slowly.

In another steel recipient again equipped with a stirrer the talc, the titanium dioxide, the precipitated silica and the curcumin are dispersed in 4.0 l of deionized water. The resulting suspension is poured into the arginine Shellac solution, washing the recipient with about 1.0 l of deionized water, then diluting with another 4.0 l of deionized water.

The enteric coating is carried out at a temperature of 45° C., once the gastroresistant coating is complete, it is left to dry for another 10 minutes again at 45° C. Finally, it is necessary to wait for the temperature to lower to 32-33° C. so as to be able to start emptying the coating pan, taking care to conserve the capsules in suitable bags that are impermeable to humidity. All of the tests foreseen by the quality specifications are also carried out on them.

TABLE 40

Stress test of Batches 046 and 047-30 mg lansoprazole capsules (quali/quantitative composition of Example 19)

| Batch (T/t)[1] | Humidity % (K.F.) | Total impurities | Count mg/cps | Resistance to gastric juice at pH 1.2[2] (minutes) | Disintegration time at pH 6.8[2] (minutes) |
|---|---|---|---|---|---|
| 046 (20/0) | 0.45 | 0.21 | 30.6 | 60.00 | 22.00 |
| 046A (40/1) | 0.44 | 0.22 | 30.5 | 60.00 | 22.00 |
| 046B (40/3) | 0.65 | 0.23 | 30.3 | 60.00 | 19.00 |
| 046C (40/6) | 0.55 | 0.21 | 30.2 | 60.00 | 19.00 |
| 047 (20/0) | 0.65 | 0.22 | 30.4 | 60.00 | 20.00 |
| 047A (40/1) | 0.66 | 0.26 | 30.2 | 60.00 | 20.00 |
| 047B (40/3) | 0.76 | 0.31 | 29.9 | 60.00 | 22.00 |
| 047C (40/6) | 0.68 | 0.32 | 29.8 | 60.00 | 22.00 |

[1]Temperature (° C.)/time (months);
[2]Disintegration test according to USP current edition.

The data in Table 40 shows that in the presence of sodium starch glycolate, the disintegration times at pH 6.8 are within specifications according to the disintegration test described in USP current edition and the variation of the disintegration again at pH 6.8 is constant over time after the samples are conserved at 40° C. for 6 months.

TABLE 41

Shelf life of Batch 048-30 mg lansoprazole capsules (quali/quantitative composition of Example 19)

| Batch (T/t)[1] | Humidity % (K.F.) | Total impurities | Count mg/cps | Resistance to gastric juice at pH 1.2[2] (minutes) | Disintegration time at pH 6.8[2] (minutes) |
|---|---|---|---|---|---|
| 048(20/0) | 0.23 | 0.34 | 30.33 | 60.00 | 20.00 |
| 048A (25/3) | 0.32 | 0.30 | 30.12 | 60.00 | 22.00 |
| 048B (25/6) | 033 | 0.32 | 30.11 | 60.00 | 20.00 |
| 048C (25/12) | 0.34 | 0.30 | 29.99 | 60.00 | 21.00 |

[1]Temperature (° C.)/time (months);
[2]Disintegration test according to USP current edition.

Example 20: 30 mg Gastroresistant Lansoprazole Capsules

| | |
|---|---|
| A. Lansoprazole | 30.00 mg |
| B Microcrystalline cellulose | 176.00 mg |
| C. Mannitol | 80.00 mg |
| D. Sorbitol | 150.00 mg |
| E. Silicon dioxide | 2.00 mg |
| F. Magnesium stearate | 2.00 mg |
| Net capsule weight | 434.00 mg |
| G. Arginine Shellac | 30.00 mg |
| H. Titanium dioxide | 5.00 mg |
| I. Talc | 10.00 mg |
| L. Triethyl citrate | 5.00 mg |
| M. Precipitated silica | 2.00 mg |
| Total capsule weight (including capsule weight) | 692.00 mg |

TABLE 42

Stress test of Batches 049 and 050-30 mg lansoprazole capsules (quali/quantitative composition of Example 20)

| Batch (T/t)[1] | Humidity % (K.F.) | Total impurities | Count mg/cps | Resistance to gastric juice at pH 1.2[2] (minutes) | Disintegration time at pH 6.8[2] (minutes) |
|---|---|---|---|---|---|
| 049 (20/0) | 0.43 | 0.32 | 30.3 | 60.00 | 33.00 |
| 049A (40/1) | 0.45 | 0.30 | 30.2 | 60.00 | 50.00 |
| 049B (40/3) | 0.56 | 0.28 | 30.3 | 60.00 | 60.00 |
| 049C (40/6) | 0.73 | 0.34 | 29.5 | 60.00 | 64.00 |
| 050 (20/0) | 0.73 | 0.27 | 30.5 | 60.00 | 37.00 |
| 050A (40/1) | 0.76 | 0.29 | 30.3 | 60.00 | 48.00 |
| 050B (40/3) | 0.87 | 0.33 | 30.7 | 60.00 | 53.00 |
| 050C (40/6) | 0.88 | 0.37 | 29.9 | 60.00 | 68.00 |

[1]Temperature (° C.)/time (months);
[2] Disintegration test according to USP current edition.

The data in Table 42 shows that in the absence of sodium starch glycolate, the disintegration times at pH 6.8 (according to USP current edition) are considerably longer at time zero, and the variation thereof again at pH 6.8 is not constant over time after the samples are conserved at 40° C. for 6 months.

TABLE 43

Shelf life of Batch 051- 30 mg lansoprazole capsules without sodium starch glycolate (quali/quantitative composition of Example 20)

| Batch (T/t)[1] | Humidity % (K.F.) | Total impurities | Count mg/cps | Resistance to gastric juice at pH 1.2[2] (minutes) | Disintegration time at pH 6.8[2] (minutes) |
|---|---|---|---|---|---|
| 051 (20/0) | 0.44 | 0.36 | 31.03 | 60.0 | 33.00 |
| 051A (25/3) | 0.55 | 0.55 | 31.00 | 60.0 | 44.00 |
| 051B (25/6) | 0.63 | 0.43 | 30.11 | 60.0 | 51.00 |
| 051C (25/12) | 0.65 | 0.35 | 29.89 | 60.0 | 64.00 |

[1]Temperature (° C.)/time (months);
[2]Disintegration test according to USP current edition.

Example 21: 500 mg Gastroresistant Lactic Ferments Capsules

| | | |
|---|---|---|
| A. Lactic ferments | 500.00 | mg |
| B Microcrystalline cellulose | 20.00 | mg |
| C. calcium phosphate dihydrate | 50.00 | mg |
| D. Magnesium stearate | 20.00 | mg |
| Net capsule weight | 590.00 | mg |
| E. Arginine Shellac | 30.00 | mg |
| F. Sodium starch glycolate | 6.0 | mg |
| G. Titanium dioxide | 5.00 | mg |
| H. Talc | 10.00 | mg |
| I. Triethyl citrate | 5.00 | mg |
| L. Precipitated silica | 2.00 | mg |
| Total capsule weight (including capsule weight) | 648 | mg |

TABLE 44

Stress test of Batches 052 and 053-500 mg lactic ferments capsules (quali/quantitative composition of Example 21)

| Batch (T/t)[1] | Humidity % (K.F.) | Total impurities | Count mg/cps | Resistance to gastric juice at pH 1.2[2] (minutes) | Disintegration time at pH 6.8[2] (minutes) |
|---|---|---|---|---|---|
| 052 (20/0) | 0.32 | 3.33 | 2.50 ml | 60.00 | 20.00 |
| 052A (40/1) | 0.28 | 11.45 | 1.10 ml | 60.00 | 20.00 |
| 052B (40/3) | 0.39 | 23.84 | 0.34 ml | 60.00 | 21.00 |
| 052C (40/6) | 0.38 | 38.48 | 0.02 ml | 60.00 | 21.00 |
| 053 (20/0) | 0.30 | 4.45 | 2.56 ml | 60.00 | 20.00 |
| 053A (40/1) | 0.57 | 13.45 | 1.20 ml | 60.00 | 20.00 |
| 053B (40/3) | 0.39 | 26.74 | 0.43 ml | 60.00 | 22.00 |
| 053C (40/6) | 0.45 | 36.75 | 0.03 ml | 60.00 | 22.00 |

[1]Temperature (° C.)/time (months);
[2]Disintegration test according to USP current edition.

The data in Table 44 shows that, for film-coated lactic ferments capsules with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 45

Shelf life of Batch 054 1000 mg lactic ferments capsules (quali/quantitative composition of Example 21)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 054 (20/0) | 0.33 | 3.67 | 2.80 ml | 60.00 | 20.00 |
| 054A (25/3) | 0.62 | 5.45 | 1.20 ml | 60.00 | 28.00 |
| 054B (25/6) | 0.41 | 8.76 | 0.90 ml | 60.00 | 22.00 |
| 054C (25/12) | 0.53 | 14.03 | 0.06 ml | 60.00 | 23.00 |

[1]Temperature (° C.)/time (months);
[2]Disintegration test according to USP current edition.

Example 22: 500 mg Gastroresistant Lactic Ferments Capsules without Sodium Starch Glycolate

| | | |
|---|---|---|
| A. Lactic ferments | 500.00 | mg |
| B Microcrystalline cellulose | 26.00 | mg |
| C. calcium phosphate dihydrate | 50.00 | mg |
| D. Magnesium stearate | 20.00 | mg |
| Net capsule weight | 590.00 | mg |
| E. Arginine Shellac | 30.00 | mg |
| F. Titanium dioxide | 5.00 | mg |
| G. Talc | 10.00 | mg |
| H. Triethyl citrate | 5.00 | mg |
| I. Precipitated silica | 2.00 | mg |
| Total capsule weight (including capsule weight) | 648 | mg |

TABLE 46

Stress test of Batches 055 and 056 500 mg lactic ferments capsules without sodium starch glycolate (quali/quantitative composition of Example 22

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 055 (20/0)  | 0.34 | 5.78  | 2.30 ml | 60.00 | 32.00 |
| 055A (40/1) | 0.36 | 18.38 | 1.30 ml | 60.00 | 38.00 |
| 055B (40/3) | 0.34 | 29.47 | 0.99 ml | 60.00 | 46.00 |
| 055C (40/6) | 0.56 | 38.99 | 0.02 ml | 60.00 | 66.00 |
| 056 (20/0)  | 0.66 | 4.99  | 2.60 ml | 60.00 | 35.00 |
| 056A (40/1) | 0.40 | 16.86 | 1.68 ml | 60.00 | 48.00 |
| 056B (40/3) | 0.56 | 33.54 | 0.88 ml | 60.00 | 59.00 |
| 056C (40/6) | 0.54 | 42.32 | 0.08 ml | 60.00 | 66.00 |

[1]Temperature (° C.)/time (months);
[2]Disintegration test according to USP current edition.

The data in Table 46 shows that the film-coated lactic ferments capsules without the presence of sodium starch glycolate in the film have considerably longer disintegration times at pH 6.8 (according to USP current edition) at time zero, and the variation thereof again at pH 6.8 is not constant over time after the samples have been conserved at 40° C. for 6 months.

TABLE 47

Shelf life of Batch 057 500 mg lactic ferments capsules without sodium starch glycolate (quali/quantitative composition of Example 22)

| Batch (T/t)[1] | Humidity % (K.F.) | Total impurities | Count mg/cpr | Resistance to gastric juice at pH 1.2[2] (minutes) | Disintegration time at pH 6.8[2] (minutes) |
|---|---|---|---|---|---|
| 057 (20/0)   | 0.34 | 6.00  | 2.30 ml | 60.00 | 36.00 |
| 057A (25/3)  | 0.46 | 8.83  | 2.00 ml | 60.00 | 48.00 |
| 057B (25/6)  | 0.68 | 10.35 | 1.89 ml | 60.00 | 4900  |
| 057C (25/12) | 0.65 | 18.83 | 1.55 ml | 60.00 | 62.00 |

[1]Temperature (° C.)/time (months);
[2]Disintegration test according to USP current edition.

Example 23: 11.0 mg NADH/Gram Gastroresistant Pellets

| DESCRIPTION OF THE COMPONENTS | | AMOUNT PER GRAM |
|---|---|---|
| Active ingredient | | |
| A) NADH | mg | 11.00 |
| B) Neutral saccharose pellets | mg | 810.00 |
| C) Sorbitol | mg | 490.0 |
| G) Talc | mg | 40.00 |
| Weight of the core pellets | mg | 910.00 |
| H) Arginine schellac | mg | 50.00 |
| I) Sodium starch glycolate | mg | 2.00 |
| L) Titanium dioxide | mg | 10.00 |
| M) Colloidal silica, anhydrous | mg | 2.00 |
| N) Talc | mg | 20.00 |
| O) Glycerol | mg | 6.00 |
| Overall weight of the pellets | mg | 1000.00 |

TABLE 48

Stress test of Batches 058 and 059 11.0 mg NADH pellets (quali/quantitative composition of Example 23)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 058 (20/0)  | 3.44 | 1.76 | 10.93  | 60.00 | 22.00 |
| 058A (40/1) | 3.67 | 2.43 | 10.68  | 60.00 | 23.00 |
| 058B (40/3) | 3.94 | 2.67 | 10.22  | 60.00 | 22.00 |
| 058C (40/6) | 3.56 | 3.98 | 9.91   | 60.00 | 23.00 |
| 058 (20/0)  | 3.34 | 1.59 | 10.89  | 60.00 | 27.00 |
| 058A (40/1) | 4.56 | 1.73 | 10.45  | 60.00 | 25.00 |
| 058B (40/3) | 3.97 | 2.54 | 10.311 | 60.00 | 23.00 |
| 058C (40/6) | 3.78 | 3.22 | 9.65   | 60.00 | 24.00 |

[1]Temperature (° C.)/time (months);
[2]Disintegration test according to USP current edition;

The data in Table 48 shows that, for 11 mg film-coated NADH pellets with the presence of sodium starch glycolate in the film, the disintegration times at pH 6.8 are within specifications according to the disintegration test described in USP current edition and the variation of the disintegration again at pH 6.8 is constant over time after the samples are conserved at 40° C. for 6 months.

TABLE 49

Shelf life of Batch 059 11.0 mg NADH pellets (quali/quantitative composition of Example 23)

| Batch (T/t)[1] | Humidity % (K.F.) | NAD[2] (%) | NADH | Resistance to gastric juice at pH 1.2[2] (minutes) | Disintegration time at pH 6.8[2] (minutes) |
|---|---|---|---|---|---|
| 059 (20/0)   | 3.23 | 1.78 | 10.88 | 60.00 | 24.00 |
| 059A (25/3)  | 5.44 | 2.89 | 10.11 | 60.00 | 23.00 |
| 059B (25/6)  | 5.97 | 2.99 | 10.22 | 60.00 | 22.00 |
| 059C (25/12) | 6.89 | 3.78 | 9.99  | 60.00 | 20.00 |

[1]Temperature (° C.)/time (months);
[2]Disintegration test according to USP current edition.

Example 24: 400 mg IONE SAMe/Gram Gastroresistant Granulate

| | |
|---|---|
| A. SAMe sulphate p-toluenesulfonate | 830.00 mg |
| B. Sorbitol | 42.000 mg |
| C. Silica (Aerosil ®) | 2.00 mg |
| D. Anhydrous microcrystalline cellulose 112 | 71.00 mg |
| E. Vegetable magnesium stearate | 12.00 mg |
| Total granule weight | 957.00 mg |
| F. Arginine Shellac ® | 21.00 mg |
| G. Titanium dioxide | 2.62 mg |
| H. Talc | 7.87 mg |
| I. Triethyl citrate | 7.87 mg |
| L. Sodium starch glycolate (explotab) | 1.50 mg |
| M. Silica (Aerosil ®) | 2.14 mg |
| Total granule weight | 1000.00 mg |

Stress test of Batches 060 and 061 400 mg/ion per gram of SAM-e granulate with sodium starch glycolate in the film-coating (quali/quantitative composition of Example 24).

TABLE 50

Stress test of Batches 060 and 061- 400 mg SAMe sulphate p-toluenesulfonate per gram granulates (quali/quantitative composition of Example 24)

| Batch (T/t)[1] | Humidity % (K.F.) | Total impurities | S,S % | Count mg/gr | Resistance to gastric juice at pH 1.2[2] (minutes) | Disintegration time at pH 6.8[2] (minutes) |
|---|---|---|---|---|---|---|
| 060 (20/0) | 1.00 | 0.34 | 82.84 | 405.85 | 60.00 | 20.00 |
| 060A (40/1) | 1.05 | 0.43 | 80.00 | 404.40 | 60.00 | 20.00 |
| 060B (40/3) | 1.10 | 0.56 | 74.73 | 402.12 | 60.00 | 20.00 |
| 060C (40/6) | 1.02 | 1.23 | 72.91 | 400.40 | 60.00 | 19.00 |
| 061 (20/0) | 1.02 | 0.67 | 82.93 | 408.33 | 60.00 | 27.00 |
| 061A (40/1) | 1.32 | 0.87 | 79.21 | 404.77 | 60.00 | 23.00 |
| 061B (40/3) | 1.21 | 1.43 | 77.92 | 402.52 | 60.00 | 22.00 |
| 061C (40/6) | 1.25 | 1.99 | 70.65 | 399.56 | 60.00 | 21.00 |

[1]Temperature (° C.)/time (months);
[2]Disintegration test according to USP current edition.

TABLE 51

Shelf life of Batch 062 400 mg SAMe sulphate p-toluenesulfonate per gram granulates (quali/quantitative composition of Example 24)

| Batch (T/t)1 | Humidity % (K.F.) | Total impurities | S,S | Count mg/gr | Resistance to gastric juice at pH 1.22 (minutes) | Disintegration time at pH 6.82 (minutes) |
|---|---|---|---|---|---|---|
| 062 (20/0) | 1.43 | 0.64 | 82.36 | 408.98 | 60.00 | 20.00 |
| 062A (25/3) | 1.33 | 0.32 | 80.53 | 407.67 | 60.00 | 23.00 |
| 062B (25/6) | 1.36 | 0.56 | 77.53 | 406.42 | 60.00 | 22.00 |
| 062C (25/12) | 1.23 | 0.65 | 74.20 | 405.62 | 60.00 | 24.00 |

1Temperature (° C.)/time (months);
2Disintegration test according to USP current edition.

The data in Tables 50 and 51 show that both the samples subjected to stress testing and those conserved at room temperature, in the presence of sodium starch glycolate in the coating film, have disintegration times at pH 6.8 within specifications according to the disintegration test described in USP current edition and the variation of the disintegration again at pH 6.8 is constant over time.

Example 25: 400 mg IONE SAMe/Gram Gastroresistant Granulates

| | |
|---|---|
| A. SAMe sulphate p-toluenesulfonate | 830.00 mg |
| B. Sorbitol | 43.50 mg |
| C. Silica (Aerosil ®) | 2.00 mg |
| D. Anhydrous microcrystalline cellulose 112 | 71.00 mg |
| E. Vegetable magnesium stearate | 12.00 mg |
| Total granule weight | 957.00 mg |
| F. Arginine Shellac ® | 21.00 mg |
| G. Titanium dioxide | 2.62 mg |
| H. Talc | 7.87 mg |
| I. Triethyl citrate | 7.87 mg |
| L. Silica (Aerosil ®) | 2.14 mg |
| Total granule weight | 1000.00 mg |

TABLE 52

Stress test of Batches 063 and 064 - 400 mg SAMe sulphate p-toluenesulfonate per gram granulates (quali/quantitative composition of Example 25)

| Batch (T/t)[1] | Humidity % (K.F.) | Total impurities | S,S % | Count mg/gr | Resistance to gastric juice at pH 1.2[2] (minutes) | Disintegration time at pH 6.8[2] (minutes) |
|---|---|---|---|---|---|---|
| 063 (20/0) | 1.23 | 0.59 | 82.45 | 407.56 | 60.00 | 29.00 |
| 063A (40/1) | 121 | 0.89 | 79.00 | 406.51 | 60.00 | 39.00 |
| 063B (40/3) | 1.32 | 0.99 | 74.33 | 404.89 | 60.00 | 50.00 |
| 063C (40/6) | 1.22 | 1.69 | 70.31 | 403.85 | 60.00 | 61.00 |
| 064 (20/0) | 1.33 | 0.55 | 83.45 | 406.99 | 60.00 | 39.00 |
| 064A (40/1) | 1.17 | 0.32 | 79.56 | 406.19 | 60.00 | 48.00 |
| 064B (40/3) | 1.29 | 1.32 | 76.32 | 405.00 | 60.00 | 59.00 |
| 064C (40/6) | 1.17 | 2.78 | 72.40 | 403.53 | 60.00 | 62.00 |

[1]Temperature (° C.)/time (months);
[2]Disintegration test according to USP current edition.

TABLE 53

Shelf life of Batch 065 400 mg SAMe sulphate p-toluenesulfonate per gram granulate (quali/quantitative composition of Example 25)

| Batch (T/t)1 | Humidity % (K.F.) | Total impurities | S,S % | Count mg/gr | Resistance to gastric juice at pH 1.2[2] (minutes) | Disintegration time at pH 6.8[2] (minutes) |
|---|---|---|---|---|---|---|
| 065 (20/0) | 1.22 | 0.53 | 82.34 | 408.45 | 60.00 | 41.00 |
| 065A (25/3) | 1.22 | 0.68 | 80.54 | 406.89 | 60.00 | 51.00 |
| 065B (25/6) | 1.34 | 0.89 | 78.45 | 405.72 | 60.00 | 60.00 |
| 065C (25/12) | 1.56 | 0.98 | 76.87 | 403.58 | 60.00 | 71.00 |

1Temperature (° C.)/time (months);
[2]Disintegration test according to USP current edition.

The data in Tables 52 and 53 show that both the samples subjected to stress testing and those conserved at room temperature, in the absence of sodium starch glycolate in the coating film, have disintegration times at pH 6.8 outside specifications according to the disintegration test described in USP current edition and the variation of the disintegration again at pH 6.8 is not constant over time.

The invention claimed is:

1. A composition which is a gastroresistant coating composition comprising a suspension or a powder to be reconstituted in water of a shellac basic amino acid salt and sodium starch glycolate and at least one physiologically acceptable excipient.

2. The composition according to claim 1, characterised in that the sodium starch glycolate is sodium starch glycolate of type A or type B and/or a mixture thereof.

3. The composition according to claim 1, characterised in that said composition is a coating composition for solid oral formulations in the form of tablets, capsules, pellets, granules and/or microgranules.

4. The composition according to claim 1, characterised in that said composition is in the form of an aqueous suspension.

5. The composition according to claim 1 wherein the coating composition is in the form of a spray suspension.

6. The composition according to claim 1, characterised in that said basic amino acid is selected from among arginine, lysine, ornithine and/or a mixture thereof.

7. The composition according to claim 6, characterised in that said basic amino acid is arginine.

8. The composition according to claim 1, characterised in that sodium starch glycolate is in form of powder with a granulometry comprised between 0.5 and 200 micron.

9. The composition according to claim 8, characterised in that sodium starch glycolate is in form of powder with a granulometry comprised between 10 and 50 micron.

10. The composition according to claim 1, characterised in that the shellac basic amino acid salt is contained in an amount between 1 and 99% by weight with respect to the total weight.

11. The composition according to claim 10, characterised in that the shellac basic amino acid salt and sodium starch glycolate are present in equal amounts.

12. The composition according to claim 10, characterised in that shellac basic amino acid salt thereof is contained in an amount between 50 and 95% by weight with respect to the total weight.

13. The composition according to claim 1, characterised in that sodium starch glycolate is contained in an amount between 0.05 and 70% by weight with respect to the total weight.

14. The composition according to claim 13, characterised in that sodium starch glycolate is contained in an amount 0.1% and 50% by weight with respect to the total weight.

15. The composition according to claim 1, characterised in that at least one additional physiologically acceptable excipient is selected from among plasticizers, suspension agents or glidants and/or dilutants.

16. The composition according to claim 15, characterised in that said suspension agents or glidants are selected from among precipitated silica, talc and/or a mixture thereof.

17. The composition according to claim 15, characterised in that said dilutants are selected from among talc, titanium dioxide and/or a mixture thereof.

18. The composition according to claim 15, characterised in that said plasticizers are selected from among triethyl citrate, polyethylene glycol, polypropylene glycol, glycerol monostearate, polyols, glycerine, vegetable oils and/or a mixture thereof.

19. The composition according to claim 18, characterised in that said plasticizers are contained in an amount between 2 and 50% by weight with respect to the total weight.

20. The composition of claim 1, wherein said composition is a coating of a coated solid oral formulation.

21. The composition according to claim 20, wherein said coated solid oral formulation is in the form of tablets, capsules, pellets, granules and/or microgranules.

22. The composition according to claim 10, wherein said coated solid oral formulation contains at least one active ingredient and/or nutraceutical, dietetic or food supplement and at least one physiologically acceptable adjuvant.

23. The composition according to claim 22, characterised in that said at least one active ingredient and/or nutraceutical, dietetic or food supplement of said coated solid oral formulation is selected from among SAMe (S-adenosyl methionine) and/or physiologically acceptable salts thereof, lansoprazole, pantoprazole, ibuprofen, lactic ferments, NADH, SOD, nattokinase.

24. The composition according to claim 22, characterised in that said at least one active ingredient and/or nutraceutical, dietetic or food supplement of said coated solid oral formulation is selected from SAMe and/or physiologically acceptable salts thereof.

25. A process for preparing a coating composition, said process comprising the steps of:
  a) preparing a solution of shellac basic amino acid salt thereof, solution A;
  b) preparing an aqueous suspension of sodium starch glycolate, suspension B;
  c) mixing solution A and suspension B.

26. The process according to claim 25, characterised in that in step a) said shellac and/or a salt thereof is dissolved in a polar solvent comprising a $C_1$-$C_4$ alcohol, water, and/or in a mixture thereof.

27. The process according to claim 25, characterised in that in step a) said shellac basic amino acid salt thereof is dissolved in a polar solvent.

28. The process according to claim 27, characterised in that said polar solvent is water.

29. The process according to claim 25, characterised in that said process is carried out at a temperature comprised between 50 and 100° C.

30. The process according to claim 29, characterised in that said process is carried out at a temperature comprised between 50 and 80° C.

* * * * *